US011896803B2

(12) United States Patent
Fleischer

(10) Patent No.: US 11,896,803 B2
(45) Date of Patent: Feb. 13, 2024

(54) ELECTROCARDIOGRAM (ECG) ELECTRODES HAVING BIO-POTENTIAL ELECTRODES

(71) Applicant: MEDICUS ENGINEERING APS, Aarhus N (DK)

(72) Inventor: Jesper Fleischer, Hojbjerg (DK)

(73) Assignee: MEDICUS ENGINEERING APS, Aarhus N (DK)

( * ) Notice: Subject to any disclaimer, the term of this patent is extended or adjusted under 35 U.S.C. 154(b) by 609 days.

(21) Appl. No.: 15/539,137

(22) PCT Filed: Dec. 22, 2015

(86) PCT No.: PCT/IB2015/059902
§ 371 (c)(1),
(2) Date: Jun. 22, 2017

(87) PCT Pub. No.: WO2016/103193
PCT Pub. Date: Jun. 30, 2016

(65) Prior Publication Data
US 2019/0209776 A1    Jul. 11, 2019

Related U.S. Application Data

(60) Provisional application No. 62/095,195, filed on Dec. 22, 2014.

(51) Int. Cl.
*A61B 5/25* (2021.01)
*A61M 5/172* (2006.01)
(Continued)

(52) U.S. Cl.
CPC ......... *A61M 5/1723* (2013.01); *A61B 5/0531* (2013.01); *A61B 5/282* (2021.01);
(Continued)

(58) Field of Classification Search
CPC ................ A61M 5/1723; A61M 5/142; A61M 2005/14208; A61B 5/04085;
(Continued)

(56) References Cited

U.S. PATENT DOCUMENTS 4,270,543 A * 6/1981 Tabuchi ............... A61B 5/0408
600/396
5,191,885 A    3/1993 Bilof et al.
(Continued)

FOREIGN PATENT DOCUMENTS

GB    1441622       7/1976
GB    1441622 A     7/1976
(Continued)

OTHER PUBLICATIONS

Gulichsen, Elizabeth, "Screening for Diabetic Cardiac Autonomic Neuropathy Using a New Handheld Device", Jul. 2012, vol. 6, Issue 4, pp. 965-972 (Year: 2012).*
(Continued)

*Primary Examiner* — Adam Z Minchella
(74) *Attorney, Agent, or Firm* — Dave Law Group LLC; Raj S. Dave

(57) ABSTRACT

Disclosed herein are devices, methods and systems for monitoring and detection of adverse events in a subject. In an embodiment, an insulin delivery device includes an insulin injection device in communication with a controller for controlling the insulin injection device. The controller is configured to receive a heart signal from one or more heart sensors, and a blood glucose signal from one or more blood glucose sensors. The controller is further configured to analyze changes in the heart rhythm of the subject based on the heart signal and determine, based on the changes in the heart rhythm and the blood glucose signal, whether the subject is and/or will be experiencing an adverse event.
(Continued)

Upon determination that the subject is or will be experiencing an adverse event, the controller determines one or more parameters of delivery of insulin to be delivered to the subject. Finally, the controller is configured to control the injection device to deliver insulin to the subject in accordance with the determined one or more parameters of delivery.

20 Claims, 30 Drawing Sheets

(51) Int. Cl.
*A61B 5/0531* (2021.01)
*A61M 5/142* (2006.01)
*A61B 5/282* (2021.01)

(52) U.S. Cl.
CPC ..... *A61M 5/142* (2013.01); *A61B 2562/0215* (2017.08); *A61M 2005/14208* (2013.01); *A61M 2005/14292* (2013.01); *A61M 2005/14296* (2013.01); *A61M 2230/04* (2013.01); *A61M 2230/201* (2013.01)

(58) Field of Classification Search
CPC ......... A61B 5/0531; A61B 5/02; A61B 5/024; A61B 5/0404; A61B 2562/0215
See application file for complete search history.

(56) References Cited

U.S. PATENT DOCUMENTS

| | | | | |
|---|---|---|---|---|
| 5,217,594 A * | 6/1993 | Henkens | ............... | C12Q 1/003 204/403.04 |
| 5,265,579 A * | 11/1993 | Ferrari | ................... | A61B 5/282 600/385 |
| 5,427,096 A * | 6/1995 | Bogusiewicz | ....... | A61N 1/0452 600/394 |
| 5,468,366 A * | 11/1995 | Wegner | ................. | C12Q 1/003 204/403.02 |
| 6,615,077 B1 | 9/2003 | Zhu et al. | | |
| 7,731,658 B2 | 6/2010 | Dalal et al. | | |
| 8,634,930 B2 | 1/2014 | Dalal et al. | | |
| 2003/0045806 A1* | 3/2003 | Brydon | ............... | A61B 5/0816 600/534 |
| 2006/0085049 A1* | 4/2006 | Cory | .................... | A61B 5/0536 607/48 |
| 2008/0004672 A1 | 1/2008 | Dalal et al. | | |
| 2008/0077026 A1* | 3/2008 | Banet | ..................... | A61B 5/327 600/509 |
| 2009/0048503 A1 | 2/2009 | Dalal et al. | | |
| 2009/0137890 A1 | 5/2009 | Burnes et al. | | |
| 2011/0066011 A1* | 3/2011 | Fleischer | ............... | G16H 20/30 600/301 |
| 2012/0157807 A1* | 6/2012 | Virtanen | ................ | A61B 5/276 600/372 |
| 2013/0310659 A1* | 11/2013 | Kawachi | ............ | A61B 5/02125 600/301 |
| 2014/0093832 A1* | 4/2014 | Nemeh | ................... | A61N 1/205 433/1 |
| 2014/0249438 A1 | 9/2014 | Morikawa et al. | | |
| 2014/0336491 A1* | 11/2014 | Balda | .................... | A61B 5/332 600/384 |
| 2017/0319082 A1* | 11/2017 | Sayme | ................... | A61B 5/316 |

FOREIGN PATENT DOCUMENTS

| | | |
|---|---|---|
| WO | 96/03072 | 2/1996 |
| WO | WO 96/03072 A1 | 2/1996 |
| WO | 2005/037092 | 4/2005 |
| WO | 2011/054042 | 5/2011 |
| WO | 2015/025187 | 2/2015 |

OTHER PUBLICATIONS

International Search Report and Written Opinion dated Jun. 16, 2016 in corresponding International Patent Application No. PCT/IB2015/059902.

International Preliminary Report on Patentabilty dated Jul. 6, 2017 in corresponding International Patent Application No. PCT/IB2015/059902.

International Search Report and Written Opinion dated Mar. 17, 2016 in corresponding International Patent Application No. PCT/IB2015/059899.

International Preliminary Report on Patentabilty dated Mar. 3, 2017 in corresponding International Patent Application No. PCT/IB2015/059899.

European Search Report for corresponding EP Application No. 158 21177.1, dated Nov. 29, 2018, 5 pages.

* cited by examiner

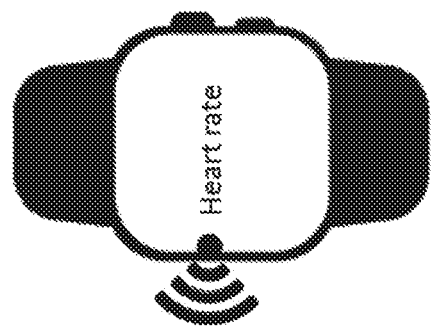
Figure 16B

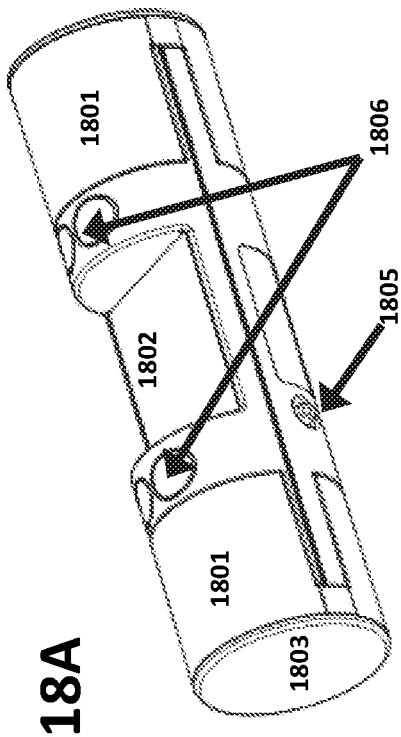
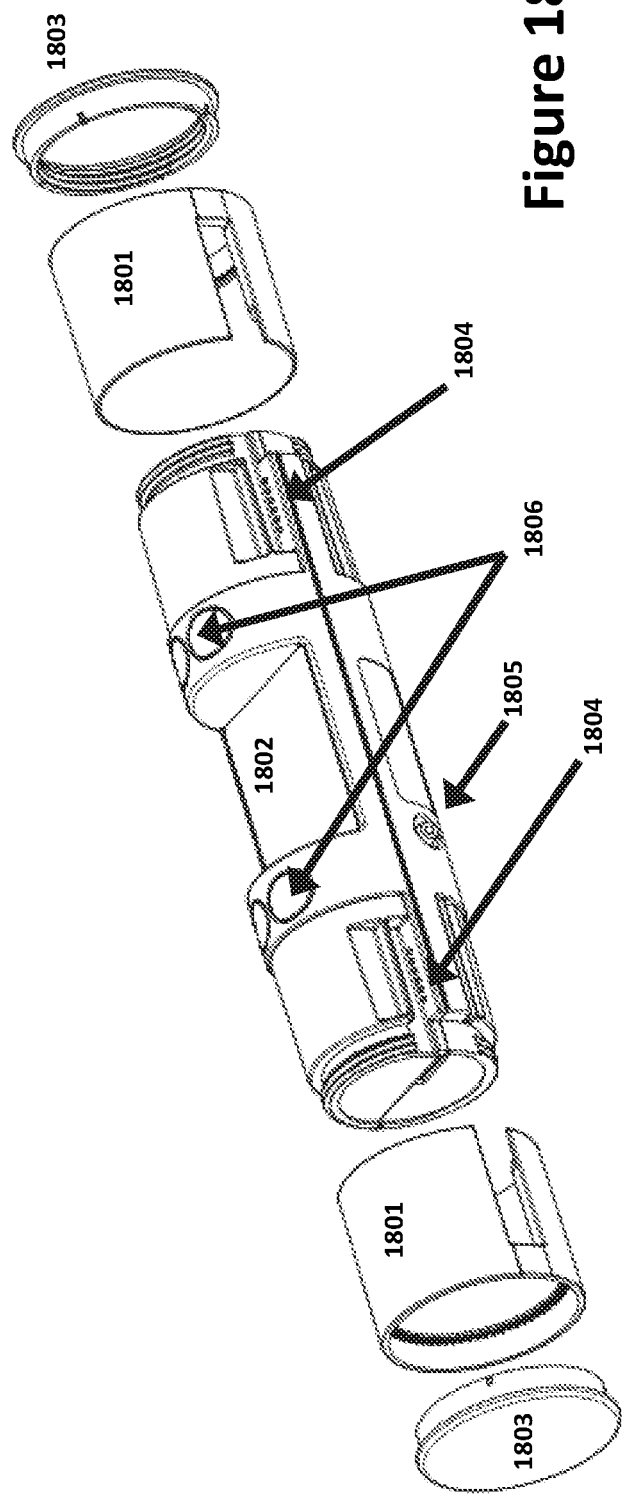
Figure 18A
Figure 18B

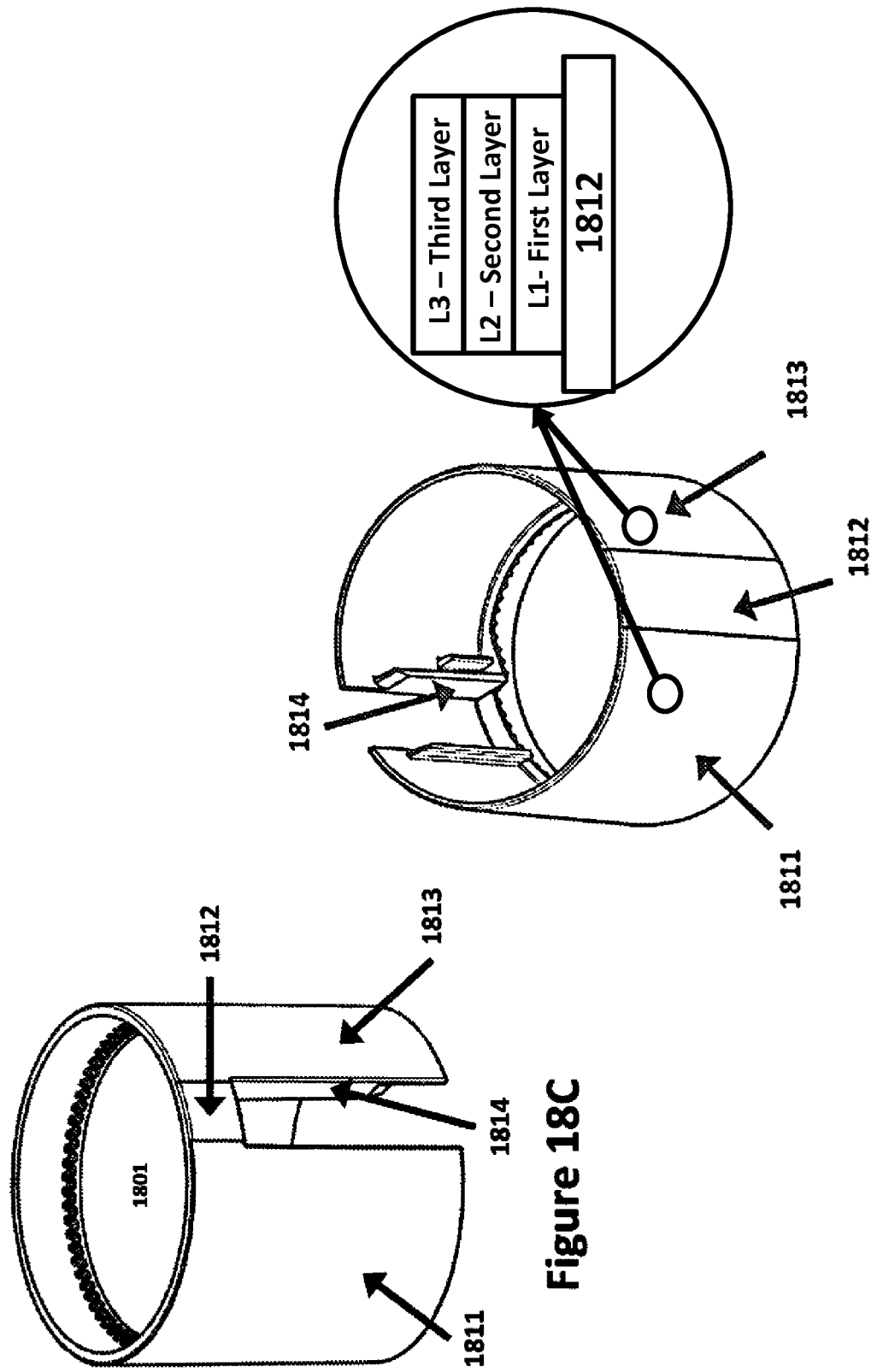

ELECTROCARDIOGRAM (ECG) ELECTRODES HAVING BIO-POTENTIAL ELECTRODES

CROSS REFERENCE TO RELATED APPLICATION

The present application is the U.S. national stage to International Patent Application No. PCT/IB2015/059902, filed Dec. 22, 2015, which claims the benefit of priority to U.S. Provisional Application No. 62/095,195, filed Dec. 22, 2014, entitled "Closed-Loop Control of Insulin Infusion", the entire content of which is incorporated herein by reference.

TECHNICAL FIELD

This disclosure relates generally to monitoring and prevention of health related conditions of a subject, and in particular, to monitoring and prevention of adverse events. This disclosure also relates generally to point-of-care device, which can test and predict changes in the autonomic nervous system of a subject, and in particular, to a method and apparatus for estimating the changes that may lead to adverse or beneficial effects in the modulation of the autonomic nervous system.

BACKGROUND

Patients with diabetes are at a constant risk of hypoglycemia. Hypoglycemia often results in an increase in physical as well as psychosocial morbidity, and is a risk factor for an increased mortality. Hypoglycemia is common in patients with type 1 diabetes (T1D). Patients trying to improve or maintain a tight glycemic control suffer from a large number of episodes of asymptomatic hypoglycemia. Plasma glucose levels may be less than 60 mg/dl (3.3 mmol/l) 10% of the time, and on average, patients with T1D suffer from two weekly incidents of symptomatic hypoglycemia. Accordingly, patients with diabetes may experience thousands of hypoglycemic events over a lifetime. In addition, these patients have a 4.7-fold excess mortality risk compared to healthy subjects. One of the approaches to mitigating these risks is the use of continuous glucose monitoring (CGM) devices to detect and warn diabetic patients about an imminent hypoglycemic event. However, problems such as false positive alarms continue to exist.

Autonomic nervous system (ANS) is a multifunctional system regulated by the sympathetic nervous system and the parasympathetic system, providing a rapidly responding mechanism to control a wide range of bodily functions such as cardiovascular, respiratory, gastrointestinal, genitor-urinary, exocrine and endocrine secretions, and microcirculation. Furthermore, ANS is involved in the regulation of immune and inflammatory processes. Autonomic dysfunction may affect both the sympathetic nervous system and the parasympathetic nervous system and may affect any organ that is innervated by the autonomic nervous system.

Heart rate (HR) and heart rate variability (HRV) are affected by both internal and external changes in, for example, breathing, blood pressure, hormone status, mental condition and physical conditions. A number of pathophysiological conditions may shift the balance in the ANS thereby decreasing or increasing stimulation to the heart's sinoatrial node, which controls HR and HRV. For example, increase in blood pressure causes arteries to stretch, thereby causing increase in baroreceptor discharge frequency which, in turn, causes increase in parasympathetic and decrease in sympathetic activity. Similarly, carotid chemoreceptor stimulation by noradrenalin leads to slowing HR and increase in rate and depth of respiration.

Recent studies have shown that screening for autonomic dysfunction the day before surgery may predict a blood pressure drop during anesthesia. Low blood pressure during anesthesia can cause critical ischemia of vital organs like the brain and heart and should be treated quickly and effective. It is shown in selected patient groups that preoperative determination of heart rate variability can predict drop in blood pressure during anesthesia induction in patients with and without diabetes. Previously conducted studies have had few participants and used equipment required special physical environment, which is why measurements are often carried out immediately before surgery. Tests of the autonomic function are not used consistently in consecutive and routine patient examinations to ensure that measurements are made at a safe time distance from the day of surgery, which will accompany mental stress, known to affect the ANS negatively. Therefore the results of these previously conducted studies are dubious.

Test for autonomic dysfunction are based on measuring of heart rate and blood pressure during controlled exercise and breathing. In order to make a diagnosis three active tests may be performed: 1) Heart rate response from laying to standing 1) Deep breathing to determine the relationship between heart rate during expiration and inspiration 3) Valsalva maneuver to determine heart rate during forced expiration and normal breathing. Under all the above mentioned active tests the external stimuli (standing, deep breathing, forced expiration) changes venous return to heart. The change in stroke volume (SV) stimulates the arterial baroreceptors by increasing/decreasing heart rate (HR) and total peripheral resistance (TPR) in an attempt to return arterial blood pressure (BP) towards a normal homeostatic level as described by the following equation: BP=SV×HR×TPR.

These three cardiovascular reflex tests combined with measurements of blood pressure are commonly regarded as a gold standard for clinical autonomic testing. If one of the three tests is abnormal, the patients are diagnosed with autonomic dysfunction; if two or more tests are abnormal, the patient is diagnosed with autonomic neuropathy. Autonomic neuropathy is a very serious disease that usually occurs as a complication of an underlying disease. The complication seen in many patient groups, such as: Neurological disorders (Multiple sclerosis, Guillaine-Barre Syndrome, spinal cord injury) or Endocrine disorders (diabetes, Growth hormone disorders, Addison disease). Several published articles demonstrating that autonomic dysfunction can predict coronary heart disease, sudden death in patients with chronic heart problems. Elimination of risk factors for autonomic dysfunction (obesity, smoking, alcohol abuse, and hypertension) will delay or slow down the progression of autonomic neuropathy. The recommended yearly screening of the autonomic nervous function is a quality assurance in clinical practice. For instance, impairment should produce an increased focus on risk factors, including—but not only—glycaemic status, lipids and blood pressure. Other closely associated diabetic complications to be considered are e.g. gastroparesis, impotence, retinopathy and neuropathy. Improvement, however, indicates that the patient's autonomic nervous system is well-functioning.

The composite physiological data may be collected with a plurality of separate measuring devices, each of which has measured the individual physiological data such as exhale pressure, blood pressure and heart rate. Furthermore, some of these external devices are not appropriate to test the autonomic nervous system, which is sensitive to by both internal and external changes in for example mental condition and physical conditions. The diagnosis has been based on simple lookup table and does not calculate a prediction based on an algorithm.

SUMMARY

In an embodiment, a system for delivering a medicament to a subject is described. The system may include one or more biomarker sensors configured to measure a level of the biomarker of a subject, one or more heart sensors configured to measure changes in a heart rhythm of the subject, an injection device configured to deliver a medicament to the subject; and a controller for controlling the injection device. The controller may be in communication with the one or more heart sensors, the one or more biomarker sensors, and the injection device. The controller may include a memory and one or more physical processors programmed with instructions. The sensor and controller may be wearable, directly attached to the skin or placed nearby the measuring/infusion area. The instructions when executed, cause the one or more physical processors to receive a biomarker signal from the one or more biomarker sensors, and a heart signal from the one or more heart sensors, analyze changes in the heart rhythm of the subject based on the heart signal, determine, based on the changes in the heart rhythm and the biomarker signal, whether there is and/or will be a change in a physiological condition of the subject, determine one or more parameters of delivery of the medicament to be delivered to the subject, and cause the injection device to deliver the medicament to the subject in accordance with the determined one or more parameters of delivery.

In an embodiment, a method for determining if a subject is and/or will be experiencing a hypoglycemic event is described. The method may include analyzing changes in a heart rhythm of a subject, analyzing a blood glucose signal from a blood glucose sensor, the blood glucose signal being an indicator of blood glucose levels of the subject, and determining, based on the changes in the heart rhythm and the blood glucose signal, whether the subject is and/or will be experiencing a hypoglycemic event.

In an embodiment, a device for insulin delivery is described. The device may include an insulin injection device in communication with a controller for controlling the insulin injection device. The controller may be configured to receive a heart signal from one or more heart sensors, and a blood glucose signal from one or more blood glucose sensors, analyze changes in the heart rhythm of the subject based on the heart signal, determine, based on the changes in the heart rhythm and the blood glucose signal, whether the subject is and/or will be experiencing a hypoglycemic event, determine, based on the determination that the subject is and/or will be experiencing a hypoglycemic event, one or more parameters of delivery of insulin to be delivered to the subject, and cause the injection device to deliver insulin to the subject in accordance with the determined one or more parameters of delivery.

In an embodiment, a medicament delivery device is described. The device may include a medicament infusion module configured to deliver the medicament to a subject, and a controller for controlling the medicament infusion module. The controller may include a memory and one or more physical processors programmed with instructions. The instructions when executed, cause the one or more physical processors to receive a biomarker signal from one or more biomarker sensors, and a heart signal from one or more heart sensors, analyze changes in a heart rhythm of the subject based on the heart signal, determine, based on the changes in the heart rhythm and the biomarker signal, whether there is and/or will be a change in a physiological condition of the subject, determine one or more parameters of delivery of the medicament to be delivered to the subject, and cause the medicament infusion device to deliver the medicament to the subject in accordance with the determined one or more parameters of delivery.

In an embodiment, a device for predicting and detecting changes in the autonomic nervous system of a subject is disclosed. The device may include one or more processors configured to (i) analyze dynamic changes in the heart rhythm of the subject during resting or during controlled exercise and breathing; (ii) analyze of one or more measurement, shown in table 4, linked to the autonomic nervous system from the subject; and (iii) combine an analysis of the dynamic changes in the heart rhythm with an analysis of the one or more measurement to determine whether there is an adverse or beneficial effects in the autonomic nervous system in a time period.

In an embodiment, a method for predicting and detecting a change in the autonomic nervous system of a subject during resting or during controlled exercise and breathing is disclosed. The method may include analyzing dynamic changes in the heart rhythm of the subject, analyzing one or more measurements linked to the autonomic nervous system obtained from the subject, and combining analysis of dynamic changes in heart rhythm of a subject with analysis of changes in one or more measurements obtained from the subject to determine whether there is an adverse or beneficial effects in the autonomic nervous system in a time period.

In an embodiment, a system for predicting and detecting an adverse or beneficial effect in the autonomic nervous system of a subject is disclosed. The system may include one or more sensors configured to measure and record a heart rhythm of the subject; one or more sensors configured to measure one or more parameters that are linked to the autonomic nervous system obtained from the subject, and one or more processors. The one or more processors are configured to: (i) analyze dynamic changes in the heart rhythm of the subject, (ii) analyze one or more measurements linked to the autonomic nervous system from the subject, and (iii) combine an analysis of the dynamic changes in the heart rhythm with an analysis of the of the one or more measurements to determine whether there is an adverse or beneficial effects in the autonomic nervous system in a time period.

BRIEF DESCRIPTION OF DRAWINGS

In the present disclosure, reference is made to the accompanying drawings, which form a part hereof. In the drawings, similar symbols typically identify similar components, unless context dictates otherwise. Various embodiments described in the detailed description, drawings, and claims are illustrative and not meant to be limiting. Other embodiments may be used, and other changes may be made, without departing from the spirit or scope of the subject matter presented herein. It will be understood that the aspects of the present disclosure, as generally described herein, and illustrated in the Figures, can be arranged, substituted, combined, separated, and designed in a wide variety of different configurations, all of which are contemplated herein.

FIGS. 16A-16F schematically show a case story.

FIGS. 18A-18B show an example for the handheld point-of-care device.

FIGS. 18C-18E show details of one of the electrodes of the handheld point-of-care device.

DETAILED DESCRIPTION

Figure 1:
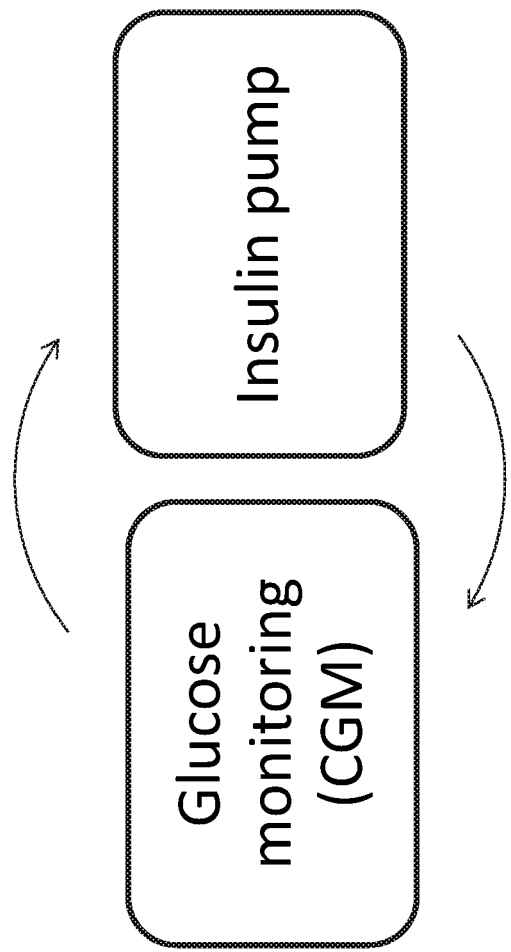
FIG. 1 depicts an illustrative schematic of a control mechanism for a close-loop artificial pancreas based on a glucose monitor signal, in accordance with the principles and aspects of the present disclosure.

Before the present methods and systems are described, it is to be understood that this disclosure is not limited to the particular processes, methods and devices described herein, as these may vary. It is also to be understood that the terminology used herein is for the purpose of describing the particular versions or embodiments only, and is not intended to limit the scope of the present disclosure which will be limited only by the appended claims. Unless otherwise defined, all technical and scientific terms used herein have the same meanings as commonly understood by one of ordinary skill in the art.

It must also be noted that as used herein and in the appended claims, the singular forms "a", "an", and "the" include plural reference unless the context clearly dictates otherwise. Thus, for example, reference to a "sensor" is a reference to one or more sensors and equivalents thereof known to those skilled in the art, and so forth. Nothing in this disclosure is to be construed as an admission that the embodiments described in this disclosure are not entitled to antedate such disclosure by virtue of prior invention. As used in this document, the term "comprising" means "including, but not limited to."

As used herein, the term "user" refers to a subject, human or animal, that uses the device or system disclosed herein. A user may be a person at risk for hypoglycemia such as, for example, a person having type I or type II diabetes.

Disclosed herein are systems of devices in close proximity to a person's body that cooperate for the benefit of the user. The communication of these devices is known as body area network (BAN), or wireless body area network (WBAN).

Disclosed herein are devices, methods and systems for monitoring and detection of information embedded in the autonomic nervous system in the heart rhythm of an individual. The methods disclosed herein may be further used during normal living (e.g., fasting, eating, activity, daily stress, etc.) because they are independent of ectopic beats, arrhythmia and artifacts which may normally limit the robustness of similar devices.

Disclosed herein are devices, methods and systems for monitoring and detection of adverse events such as hypoglycemia, hyperglycemia, or device safety issues during automated delivery of medication. The devices, method and systems disclosed herein may be further used for prevention of these events by controlled infusion of insulin in anticipation of an event, and transmitting this information to the user or a person associated with the user (e.g., a relative, or a caregiver).

An "open-loop system" e.g. a subcutaneous insulin pump with real-time continuous glucose monitoring (CGM) is currently being used for the management of type 1 diabetes in selected individuals. The limits of the open loop system are particularly seen in pediatric populations and in individuals with less motivation or with cognitive impairment. Furthermore, open-loop systems suffer from user errors, poor detection of alarms during sleep, and complacency with frequent alarming for hypoglycemia are problems with the current systems. These issues support the need for the development of control algorithms that automatically and accurately alter insulin infusion rates to achieve normal glucose levels during fasting, eating, activity, and daily stress. These and other drawbacks exist.

FIG. 1 depicts a schematic of an automated mechanical glucose-responsive sensor-guided insulin infusion system also called an artificial pancreas or a "closed loop system." A closed-loop system may include, (as depicted in FIG. 1): a continuous glucose monitoring (via a subcutaneous sensor or noninvasive e.g. Smart lens) device; a computerized closed loop controller to determine the proper insulin infusion rate and automatically adjusting insulin levels in a subject; and a subcutaneous insulin pump.

Figure 2:
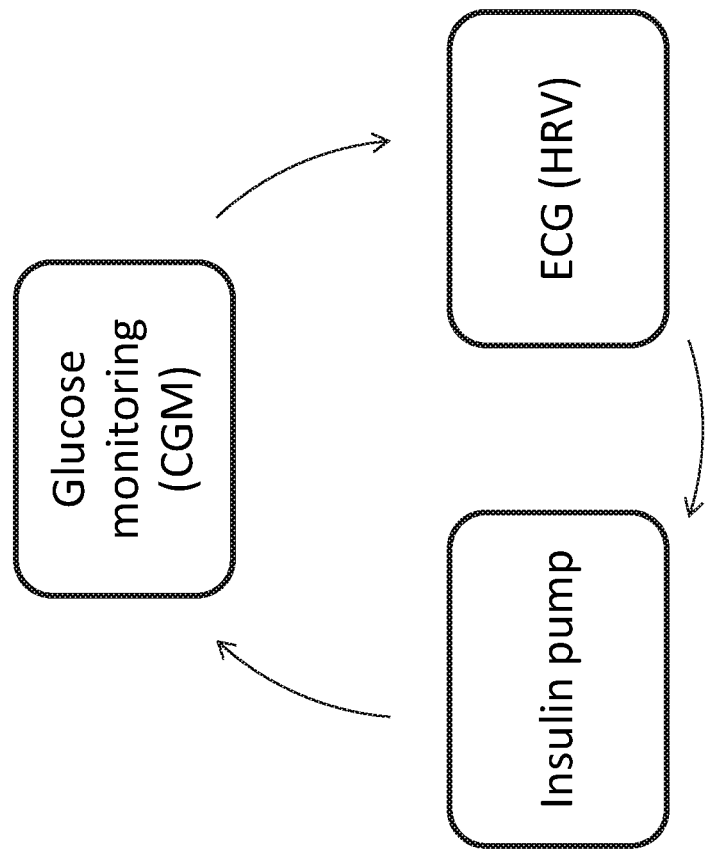
FIG. 2 depicts an illustrative schematic of a control mechanism for a closed-loop artificial pancreas based on a glucose monitor signal and a heart rate signal, in accordance with the principles and aspects of the present disclosure.

FIG. 2 depicts a schematic of a closed-loop artificial pancreas that is controlled based on a continuous glucose monitor signal and a heart rate signal. A computerized closed-loop controller determines advent of hypoglycemic events and adjusts insulin infusion rates so as to automatically adjust blood glucose levels in a patient. The insulin may be provided to the patient via, for example, a subcutaneous insulin pump.

In an embodiment, hypoglycemic events may be detected using changes in heart rate and heart rate variability (HRV) in conjunction with continuous glucose monitor signals. Advantageously, using heart rate and heart rate variability in conjunctions with continuous glucose monitoring as described herein improves detection of hypoglycemic events during normal living (e.g., during fasting, eating, activity, daily stress, etc.).

As used herein, "heart rate variability" (HRV) refers to variation in the time interval between heartbeats. HRV has been found to be a measure of the balance in the autonomic nervous system and is dependent on both internal and external changes in the body. Decreased parasympathetic nervous system activity or increased sympathetic nervous system activity results in reduced HRV. HRV may be measured using, for example, electrocardiogram, blood pressure, ballistocardiograms, pulse wave signals derived from photoplethysmograph, and so forth. In various embodiments, HRV may be measured at different sampling rates such as, for example, 0.01 Hz, 0.05 Hz, 0.1 Hz, 0.5 Hz, 1 Hz, 5 Hz, 10 Hz, 50 Hz, 100 Hz, 500 Hz, 1 kHz, and so forth or at any sampling rate between any two of these sampling rates.

By combining the complex dynamic/pattern of HRV with a surrogate measure of a biomarker it may be possible to improve the detection and prediction of a given change in a physiological condition which is measured by the biomarker surrogate. The HRV dynamic/pattern adds important information regarding the modulation of the autonomic nervous system and thereby can be used to clarify whether a change or event measured by the biomarker is of physiological significance, which could include a change or event of clinical interest that might require clinical intervention. This clarification is more significant when using a surrogate measure of a biomarker. For example, when the biomarker surrogate is CGM, there is a lag-time between CGM measurements and actual blood glucose levels (glucose levels in interstitial fluid lag behind blood glucose values) causing poor accuracy in event detection. Therefore, in terms of detection of hypoglycemia or hyperglycemia, CGM devices, have poor specificity and thus result in numerous false positive alerts. By combining pattern recognition of HRV with a CGM device the detection and prediction of hypoglycemia or hyperglycemia may be significantly improved. Besides detection and prediction of hypoglycemia or hyperglycemia the methods disclosed herein may be used in any biomarker surrogates that are influenced by the autonomic nervous system.

Figure 3:
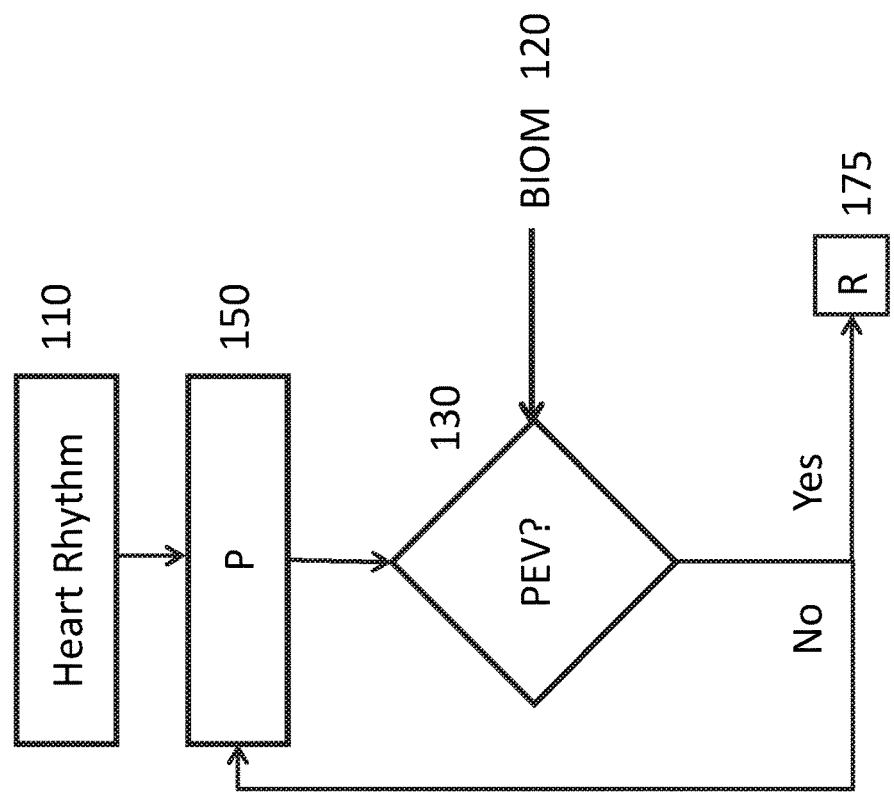
FIG. 3 depicts an illustrative process for a method of monitoring and predicting a change in a physiological condition using Heart Rate Variability (HRV) in combination with one or more biomarkers, in accordance with the principles and aspects of the present disclosure.

FIG. 3 depicts an illustrative process for a method of monitoring and predicting a change in a physiological condition using Heart Rate Variability (HRV) in combination with one or more biomarkers according to an embodiment. At block 110, HRV of a subject is measured by a sensor. The HRV data fed to a processor P which, at block 150, analyzes the HRV data based on a pre-determined algorithm. At block 130, processed HRV data is combined (using, e.g., another processor not shown in FIG. 1) with measurements relating to one or more biomarkers BIOM from one or more sensors gathered at block 120 and analyzed for change in a physiological condition. This analysis may be fed back to processor P for analysis at block 150. If the change in the physiological condition is deemed, based on a pre-determined set of criteria, a reaction R is provided at block 175.

In various embodiments, the patterns in the HRV data may be used to evaluate the clinical relevance of each data point obtained from the biomarker measurements. For example, in an embodiment, glucose measurement is used for detection of hypoglycemia. In such embodiment, glucose levels are measured periodically (e.g., every 5 minutes) and patterns in HRV data are used to determine whether a particular glucose measurement indicates an onset of hypoglycemia. In other embodiments, other biomarkers may be used and measurements obtained at a different frequency. In some embodiments, the biomarker data may undergo processing similar to the HRV data.

In various embodiments, physiological conditions may be induced under controlled clinical conditions while gathering HRV data. In many embodiments, HRV data may be gathered for up to 10 hours prior to induction of the physiological event and up to 10 hours after the induction of the physiological event. As such, incidence of various features and patterns extracted from the HRV data may be correlated with the particular physiological event being induced based on the analysis being performed.

Figure 4:
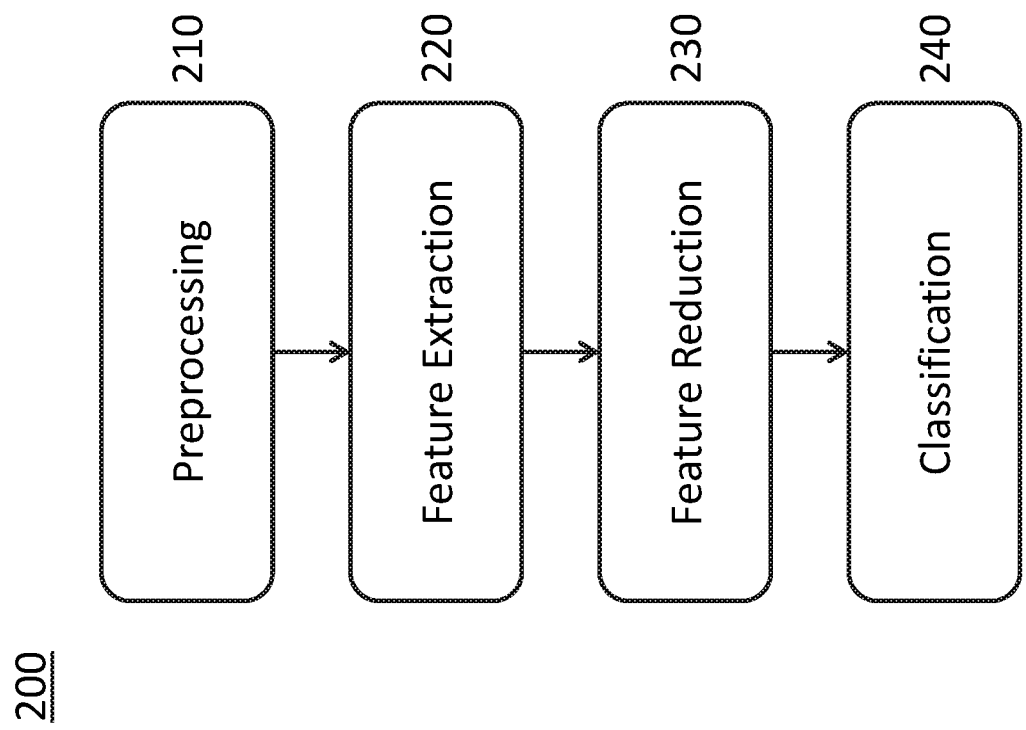
FIG. 4 depicts an illustrative pattern recognition model, in accordance with the principles and aspects of the present disclosure.

HRV of a subject may be measured using any device or method. For example, in an embodiment, HRV of a subject is measured using electrocardiogram (ECG). FIG. 4 depicts an illustrative pattern recognition model according to an embodiment. In various embodiments, analysis of HRV at block 150 may include, for example, preprocessing at block 210, feature extraction at block 220, feature reduction at block 230, and classification at block 240.

In embodiments where HRV is measured using ECG, a signal from the ECG is preprocessed, at block 210, for detection of peaks and calculation of RR-intervals. RR-interval, as used herein, is the interval between an R wave and the next R wave as measured by the ECG. The R-wave detection may be performed with various methods such as, for example, Pan and Tompkins with (a) bandpass filter, (b) differentiating, (c) squaring and (d) moving-window integration or signal energy analysis and moving-window.

In various embodiments, the verification of RR recording may be performed using one or more of the analysis tools such as, for example, Poincare Plots, Nonlinear analysis, or time-frequency analysis, and may be performed in time domain or frequency domain. Power spectra density may then be estimated using parametric or non-parametric models such as, for example, Welch's method, auto regression, periodogram, Bartlett's method, autoregressive moving average, maximum entropy, least-squares spectral analysis, and so forth.

In various embodiments, RR-intervals may be divided in epochs of several minutes. It will be understood by one skilled in the art that any time length of an epoch may be chosen and will depend on factors such as, for example, data sampling rate, processing power, memory available to the processor, efficiency of algorithms used for analysis, and so forth. In an embodiment, for example, duration of an epoch may be 5 minutes.

RR-interval outliers from each epoch may then be replaced with a mean from that particular epoch. Outliers, in some embodiments, may be defined as RR-intervals deviating 50% from previous data RR-interval or outside 3 standard deviations. Epochs may be analyzed using proprietary or commercially available tools. The analysis may be performed using one or more of analysis tools such as, for example, of Poincare Plots, Nonlinear analysis, time-frequency analysis and performed in time domain or frequency domain. Power spectra density may then be estimated using parametric or non-parametric models such as, for example, Welch's method, auto regression, periodogram, Bartlett's method, autoregressive moving average, maximum entropy, least-squares spectral analysis, and so forth.

Preprocessing of the ECG signal may be followed by feature extraction, at block 220. Preprocessed RR-interval data is sent to block 220 to find, preferably, a small number of features that are particularly distinguishing and/or informative for classification of the features based on physiological conditions being induced. In various embodiments, features extracted, at block 220, from the RR-interval data up to several epochs prior to the physiological event may be used for calculating various features. In some embodiments, analysis may be performed on data, for example, 10 epochs, 15 epochs, 20 epochs, 30 epochs, 40 epochs, 50 epochs, 100 epochs or any number of epochs therebetween, prior to the physiological event.

Analysis performed on the RR-interval data at block 220 may, in various embodiments, include, for example, differentiation, averaging, calculation of slope, ratios of instantaneous values, standard deviation, skewness, regression coefficients, slopes of regression ratios, and standardized moment, and so forth. Features extracted from the HRV data may include, for example, median heart rate average from particular epoch range prior to an event, or the skewness of standard deviation of normal-to-normal intervals from particular epoch range prior to an event, and so forth. In some embodiments, analysis of HRV may be performed in real-time during daily living, or in combination with control exercise or paced breathing.

RR-interval data extracted at block 220 may include a large number of different features may be evaluated for their ability to discriminate for a physiological event. Such features may then, be passed down to block 230 to be grouped to form patterns that may be indicative of a particular physiological event. At block 230, a ranking algorithm based on e.g. a t-test may be used, in some embodiments, for eliminating features that do not signify an event.

In some embodiments, the ranking algorithm may calculate an average separability criterion for each feature. Such a criterion may reflect the ability of the classification method to separate the means of any two classes of features in relation to the variance of each class. Subsequently, various features may be correlated with physiological events. Features with lowest separability may be eliminated if correlation with higher ranking features exceeds a threshold. In an embodiment, a correlation threshold of, for example, 0.7 may be used. In various embodiments, the correlation threshold may be chosen depending on the desired specificity and sensitivity of prediction of the physiological event. In many embodiments, cross-validation may be performed to reduce generalization errors.

Once the features are extracted and reduced, particular features may be chosen for their ability to predict a physiological event based on correlation factors. This is followed by classification, at block 240, of the features to correlate them with particular physiological events. Various classification models may then be used for classifying physiological events as normal or abnormal based on such features. For example, in an embodiment, non-probabilistic binary linear classifier support vector machine may be used. A skilled artisan will appreciate that other classification methods may be also used, alone or in combination. For example, linear classifier models such as Fisher's linear discriminant, logistic regression, naive Bayes classifier, Perceptron, may be used for classification. Other examples of classification models include, but are not limited to, quadratic classifiers, k-nearest neighbor kernel estimation, random forests decision trees, neural networks, Bayesian networks, Hidden Markov models, Gaussian mixture models, and so forth. In some embodiments, multi-class classification may also be used, if needed.

In an embodiment, at block 240, forward selection may be used to select a subset of features for optimal classification. This selection may be performed by including a cross-validation with, for example, 10 groups and allocating a particular number of events for training the model. Forward selection may start with no features followed by assessing each feature to find the best feature that correlates with the particular physiological event. Such feature may, then, be included in an optimal feature subset for appropriate classification. Selection of new features may be repeated until addition of new features does not result in improved predictive performance of the model.

Figure 5:
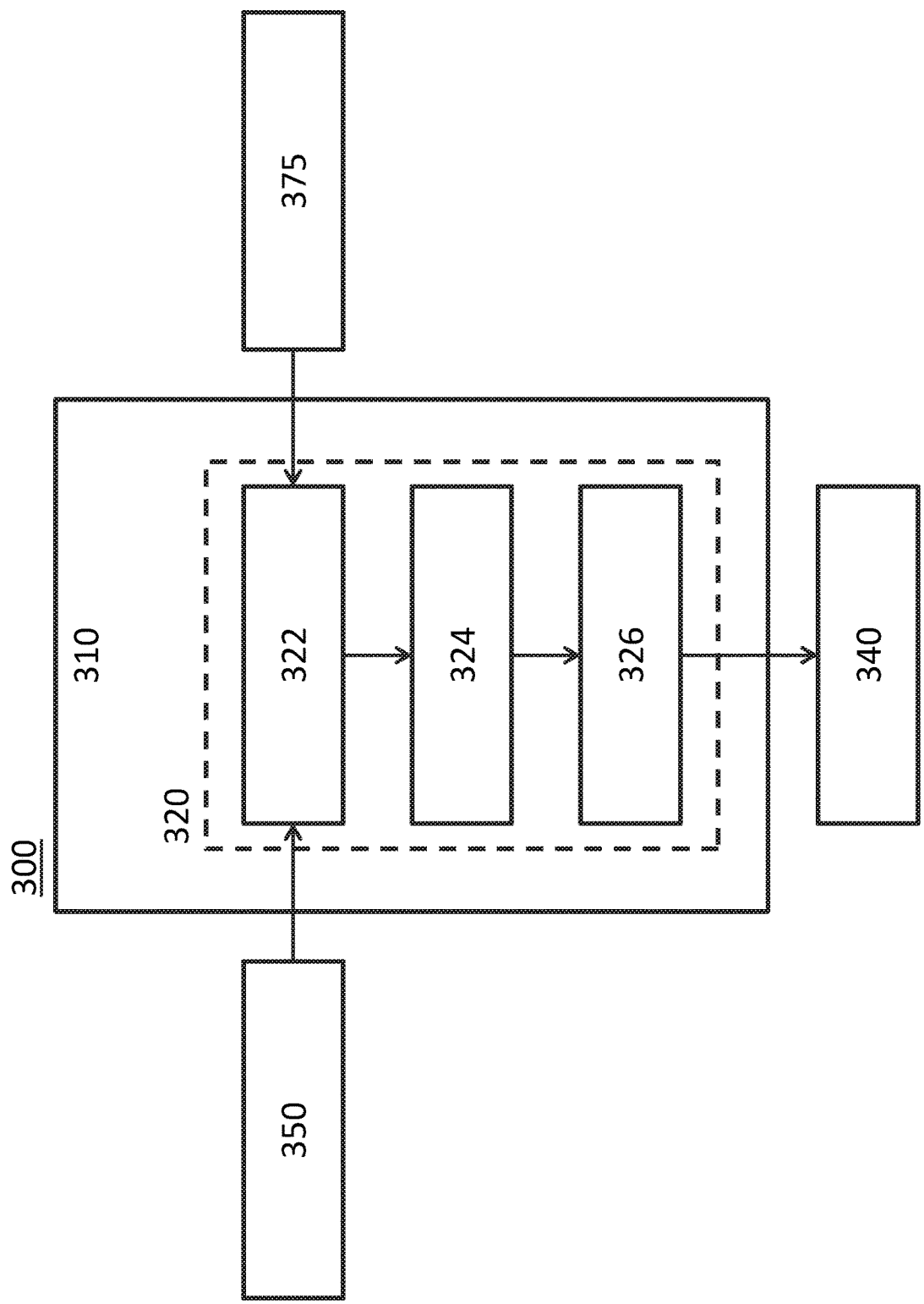
FIG. 5 depicts a block diagram of a device used for analysis of HRV data, in accordance with various aspects and principles of the present disclosure.

FIG. 5 depicts a block diagram of a device used for analysis of HRV data in accordance with various aspects and principles of the present disclosure. Device 300 used for analysis of HRV data may include processor 310 configured to run algorithm 320 that enables prediction or detection of a physiological event. Heart rhythm 350 along with at least one biomarker 375 and their time of measurement are received and analyzed by algorithm 320. In some embodiments, measurements of heart rhythm 350 and biomarker 375 may be entered manually. In other embodiments, the measurements may be transmitted automatically to processor 310 using a wired or a wireless connection to device 300. Algorithm 320 may include, calculating one or more statistical measures, at block 322, of heart rhythm 350 and biomarker 375 data. At block 324, the physiological state or change in the physiological state is estimated and analyzed for a possibility that the physiological state or change in the physiological state may be non-healthy. At block 326, an output is generated based on the analysis of block 324. For example, if it is determined, at block 324, that a change in physiological state is non-healthy, an alarm signal is generated at block 326. Device 300 may produce a reaction 340 based on the output generated at block 326. In various embodiments, reaction 340 may be a visual, audio, or audiovisual signal such as, for example, an alarm, a text message, a flashing light, and so forth.

In many embodiments, processor 310 may be part of a computer, a tablet, a smartphone, or a standalone device. In some embodiments, the device may have in-built sensors for measuring HRV data 350. For example, a smartphone having a light emitting diode (LED) capable of producing infra-red light and an optical sensor (e.g., a camera) may be able to obtain HRV data using IR thermography. In many embodiments, the device used for analyzing the HRV data may include, for example, a controlling unit (e.g., a digital signal processor or DSP), a memory (e.g., random access memory, and/or non-volatile memory), one or more sensors (e.g., IR sensors, electrodes, etc.), one or more feedback mechanisms (e.g., display, a printer, speakers, LEDs or other light sources, etc.), and/or one or more input ports. The device for analyzing HRV data may also include sensors for measuring and analyzing any other biomarker(s).

In an embodiment, HRV measurements 350 may be combined, at block 322, with measurements of blood glucose levels 375 for monitoring and prediction of hypoglycemia. In such embodiments, HRV data 350 may be combined with, e.g., blood glucose measurements 375 taken over a period of time prior to a hypoglycemic event. Patterns from the combination of HRV and blood glucose data may be used to discriminate between normoglycemia and hypoglycemia. A model may be trained by analyzing HRV features over, e.g., 10-20 epochs combined with blood glucose measurements prior to an induced hypoglycemic event. Once trained to discriminate between normoglycemic events and hypoglycemic events, the model may then be used to predict, at block 324, the occurrence of a hypoglycemic event based on HRV and blood glucose measurements.

Blood glucose data 375 may be obtained intermittently or continuously. In some embodiments, it may be possible to obtain blood glucose data using non-invasive technologies that include, for example, infra-red detection, ultrasound or dielectric spectroscopy and so forth. In many embodiments, such technologies may be integrated with equipment used for obtaining HRV data. In other embodiments, an implanted chip may be used for obtaining continuous blood glucose data.

Table 1 provides a list of biomarkers that may be used in concert with HRV for predicting and monitoring various physiological conditions.

TABLE 1

| Physiological condition | Examples of Biomarker or surrogate measure of a biomarker |
|---|---|
| Epileptic attack | EEG, EMG, motion detection |
| Asthma attack | EEG, breathing (sounds and rate) |
| Panic attack | EEG, ECG, breathing (sounds and rate), sudomotor function |
| Heart attack or event | ECG, pulse wave velocity |
| Sudden hypotension | Blood pressure |
| Sleep apnea | EEG, breathing (sounds and rate) |
| Fatigue | ECG, EMG, motion detection |
| Stress, including post-traumatic stress | EEG, bioimpedance, breathing (sounds and rate) |
| Neuropathy | Bioimpedance, nerve conduction, EEG, EMG, dolorimeter, vibration testing, motion detection |
| Dehydration | Blood pressure, bioimpedance, breathing |
| Liveness detection | Bioimpedance |
| Lie detection | Polygraph |

List of biomarkers or biomarker surrogates used for detection/prediction for physiological events/conditions (EEG-electroencephalogram; EMG-Electromyography; ECG-Electrocardiography).

Another embodiment is implemented as a program product for implementing systems and methods described herein. Some embodiments can take the form of an entirely hardware embodiment, an entirely software embodiment, or an embodiment containing both hardware and software elements. One embodiment is implemented in software, which includes but is not limited to firmware, resident software, microcode, etc.

Furthermore, embodiments can take the form of a computer program product (or machine-accessible product) accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device). Examples of a computer-readable medium include a semiconductor or solid-state memory, magnetic tape, a removable computer diskette, a random access memory (RAM), a read-only memory (ROM), a rigid magnetic disk, and an optical disk. Current examples of optical disks include compact disk-read only memory (CD-ROM), compact disk-read/write (CD-R/W), and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

The logic as described above may be part of the design for an integrated circuit chip. The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication.

The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product.

Figure 7:
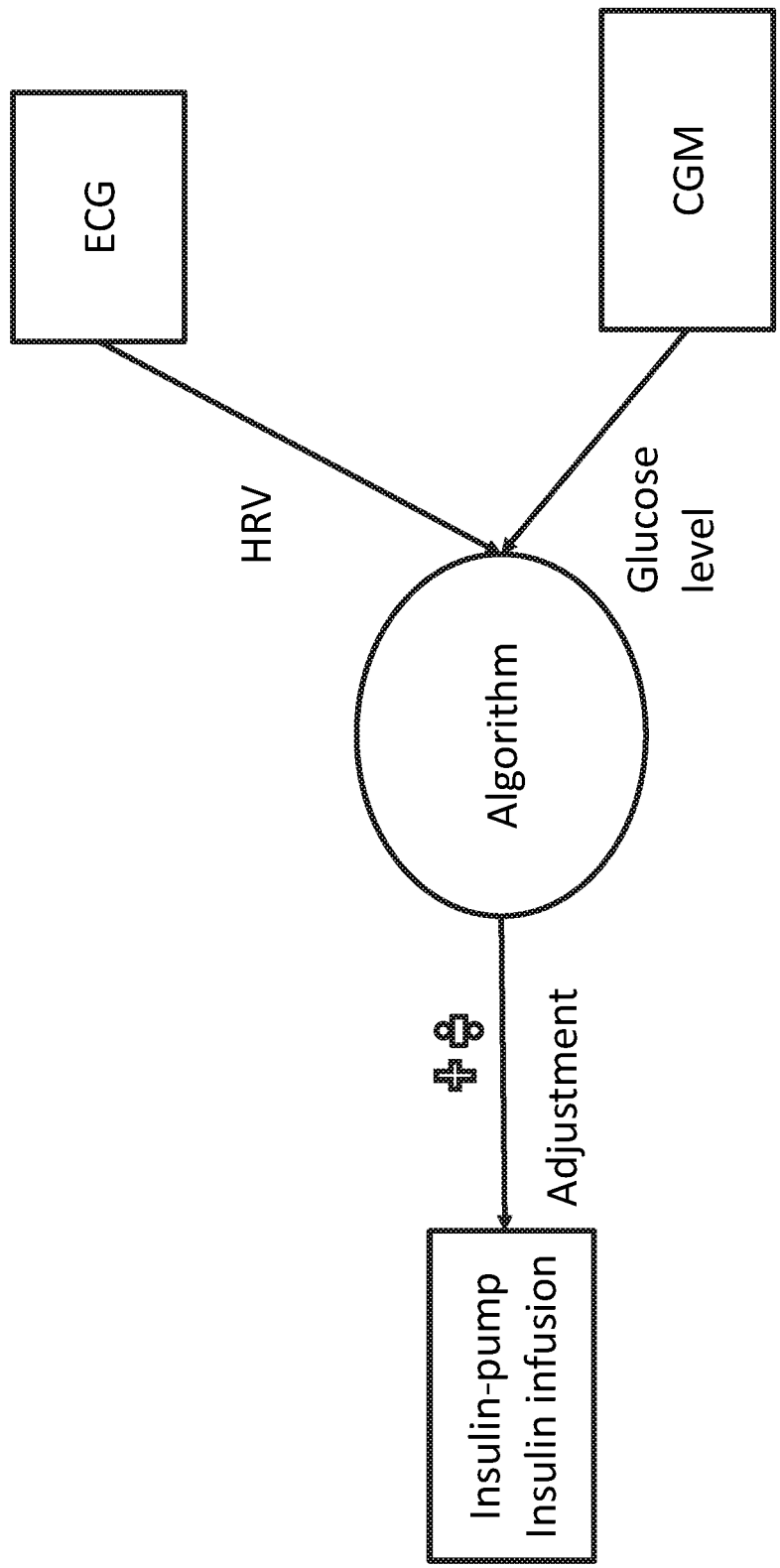
FIG. 7 depicts an illustrative schematic of a feedback mechanism for an insulin pump, in accordance with the principles and aspects of the present disclosure.

FIG. 7 depicts a feedback mechanism for controlling an insulin pump. In an embodiment, a closed-loop artificial pancreas may be implemented with a computerized controller that uses the pattern of HRV and CGM signals for controlling an infusion rate of insulin via an insulin pump. In such an embodiment, the computerized controller implements an algorithm described herein to predict onset of adverse events such as hypoglycemia, hyperglycemia, or device safety issues during automated delivery of insulin. For example, the computerized controller may shut of insulin infusion if the algorithm predicts that a hypoglycemic event is impending and send notification to the patient, an emergency responder, or a caregiver associated with the patient. In various embodiments, the controller may additionally contain a GPS tracking sensor. In such embodiments, the notification may include the location of the patient so that a caregiver or an emergency responder can locate the patient with relative ease.

Figure 8:
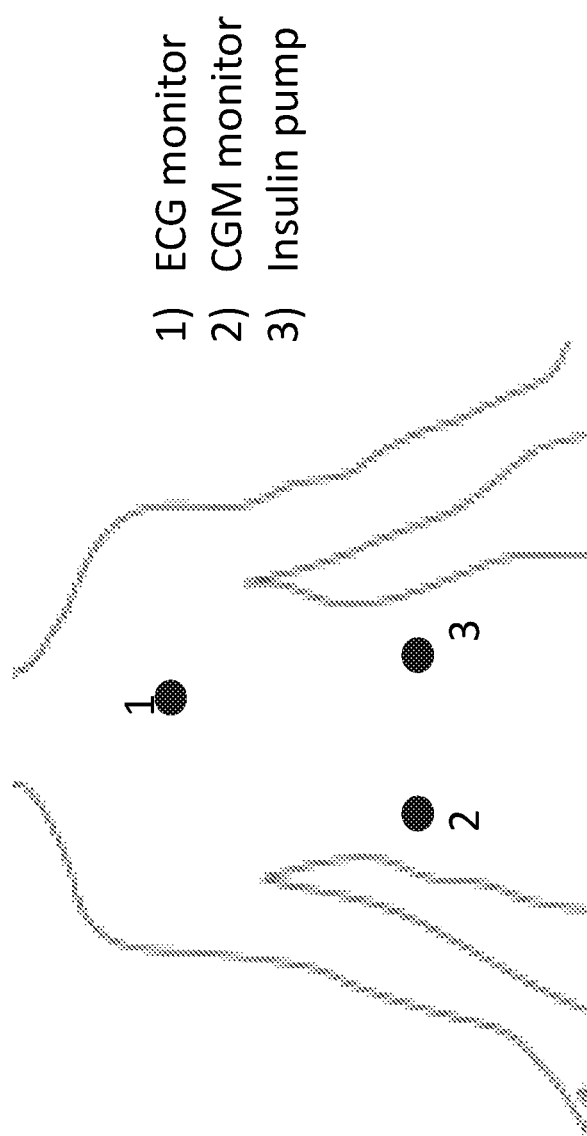
FIG. 8 depicts an illustrative schematic of a placement of glucose monitor, ECG monitor and insulin pump on a subject's body, in accordance with the principles and aspects of the present disclosure.

In an embodiment, a closed-loop artificial pancreas system may include a glucose monitor, an ECG monitor and an insulin pump placed on a subject's body. FIG. 8 depicts a relative placement of the glucose monitor, the ECG monitor and the insulin pump on the subject's body. In such an embodiment, the glucose monitor may be a continuous glucose measurement monitor, which includes sensors for collecting glucose data and electronics for analyzing the collected glucose data. The ECG monitor may include electrodes and electronics for collecting and analyzing heart rate and heart rate variability signals as described elsewhere herein. The insulin pump may include microfluidic channels for appropriately delivering insulin (e.g., through subcutaneous infusion) to the subject, and electronics for controlling the rate of flow of insulin via the microfluidic channels. The glucose monitor and the ECG monitor may be connected to the insulin pump via wired or wireless connections.

Figure 9:
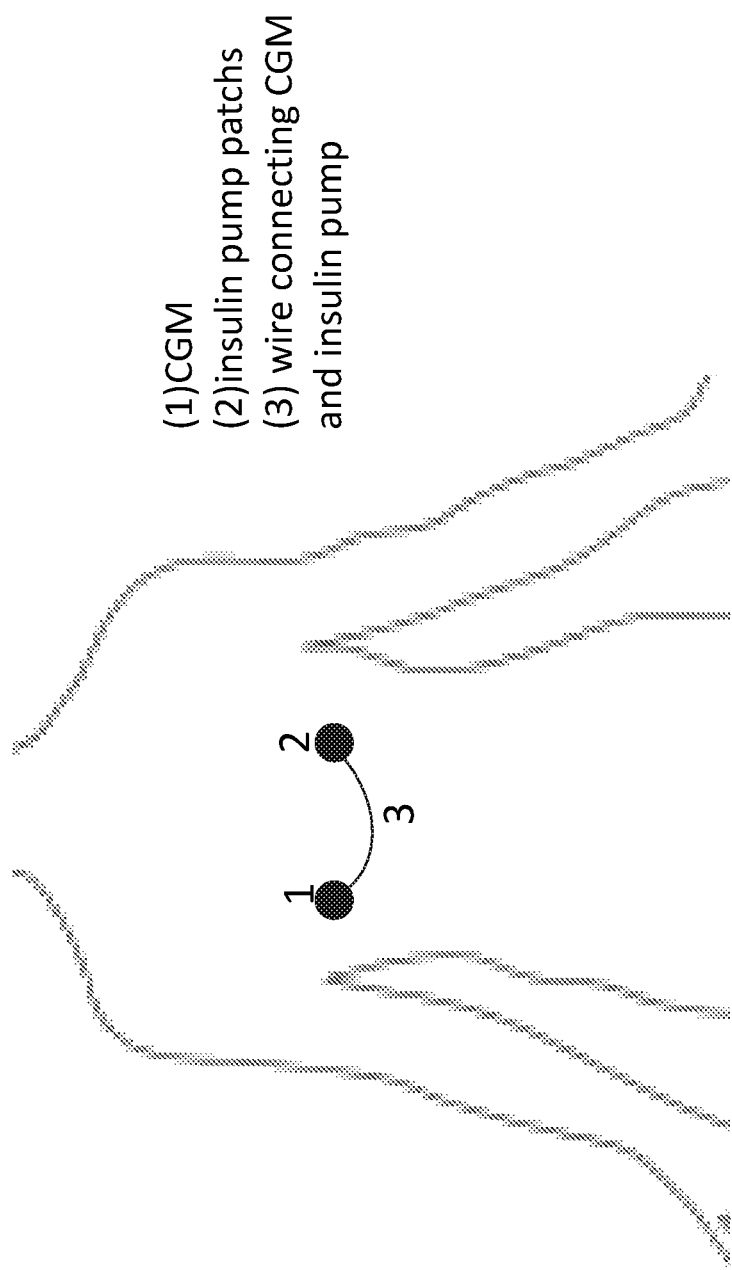
FIG. 9 depicts an illustrative schematic of a placement of glucose monitor and insulin pump patches with built-in ECG electrodes and electronics on a subject's body, in accordance with the principles and aspects of the present disclosure.

In an embodiment, a closed-loop artificial pancreas system (which, in some embodiments, may be a wearable device) may include a glucose monitor and an insulin pump having built-in ECG electrodes. FIG. 9 depicts a relative placement of the glucose monitor and the insulin pump in such an embodiment. The insulin pump of such an embodiment may include patches with built-in electrodes for ECG measurements, thereby minimizing the area of the body where the wearable device is attached, leading to better compliance and patient comfort. The glucose monitor and the insulin pump may be connected via a wired (as depicted) or a wireless connection. The electronics for analyzing the ECG and CGM data, and controllers for controlling the delivery of insulin maybe integrated within the insulin pump.

Figure 10:
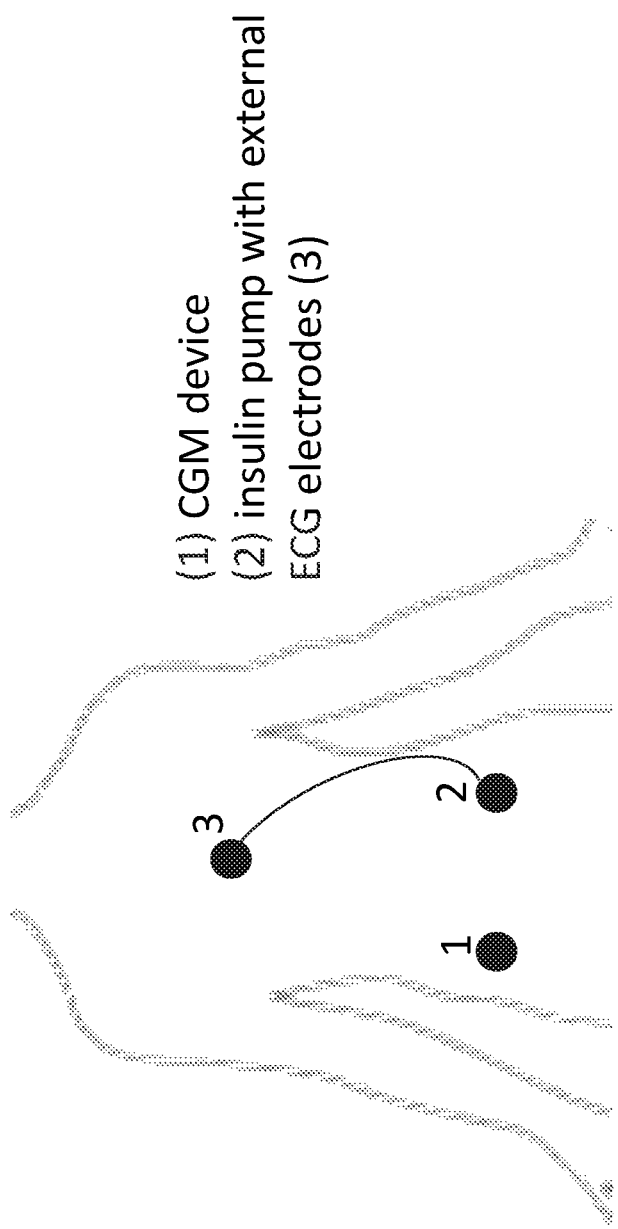
FIG. 10 depicts an illustrative schematic of a placement of glucose monitor and insulin pump with external ECG electrodes on a subject's body, in accordance with the principles and aspects of the present disclosure.

In an embodiment, the insulin pump may include electronics for collecting and analyzing the ECG data, electronics for analyzing the combination of the ECG data and the CGM data, and controllers for controlling the delivery of insulin. In such an embodiment, the ECG electrodes may be external to the insulin pump (as depicted in FIG. 10). The glucose monitor may be connected to the insulin pump via a wired or a wireless connection.

Figure 11:
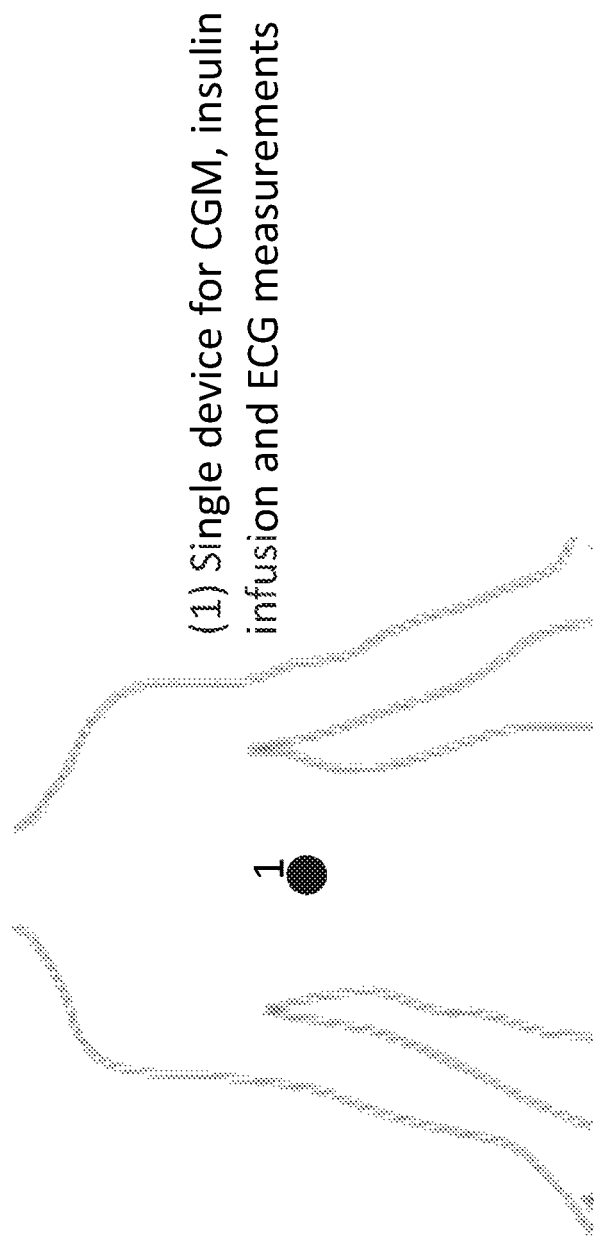
FIG. 11 depicts an illustrative schematic of a placement of a single device functioning as glucose monitor, ECG monitor and insulin pump, on a subject's body, in accordance with the principles and aspects of the present disclosure.
Figure 12:
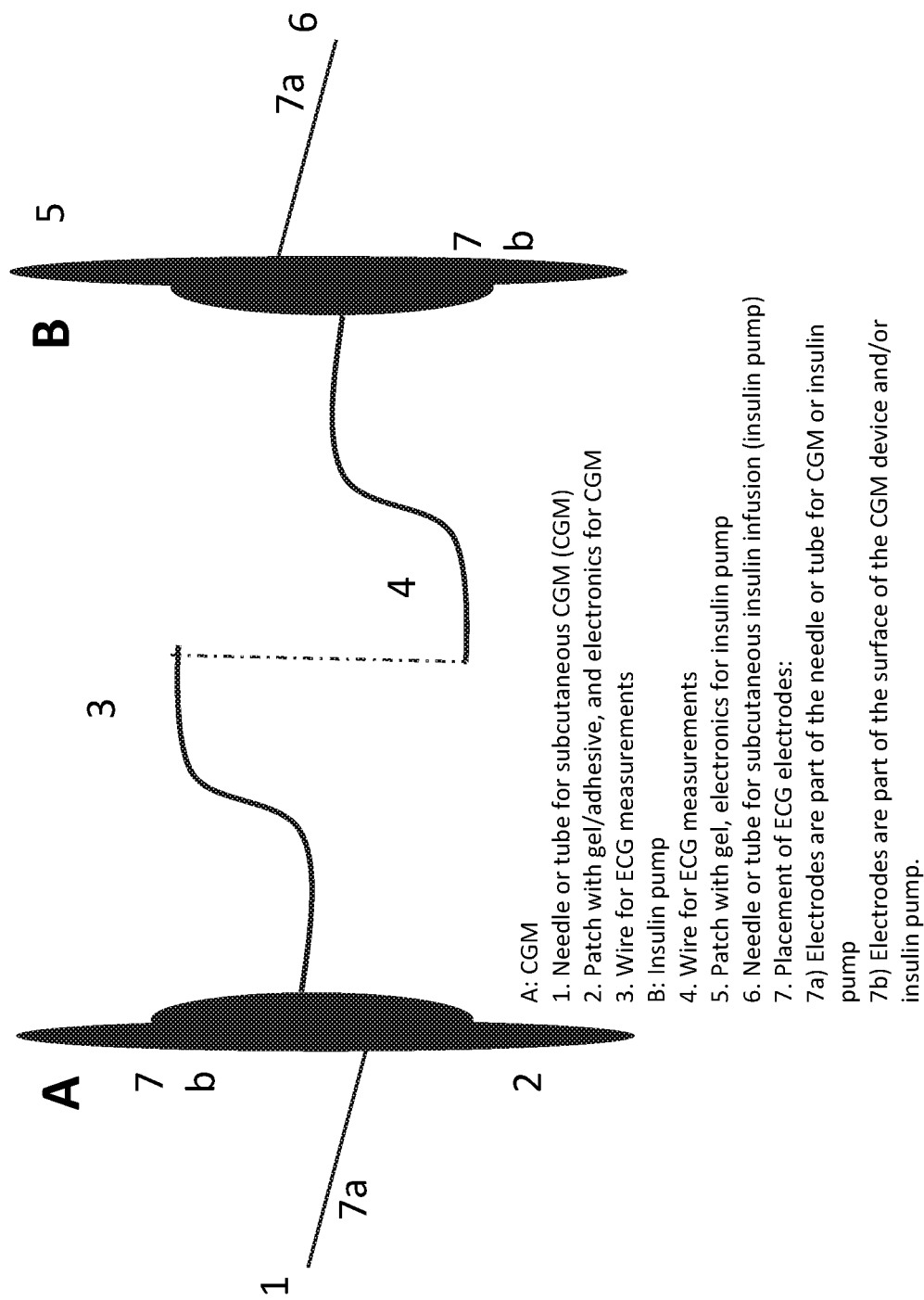
FIG. 12 depicts an illustrative schematic of a patient patch for placing a glucose monitor and insulin pump with built-in ECG electrodes, in accordance with the principles and aspects of the present disclosure.

In an embodiment, the glucose monitor, the ECG monitor, and the insulin pump may be integrated within a single device, as depicted in FIG. 11. In such an embodiment, needle(s) and/or tube(s) for subcutaneous delivery and/or measurement of insulin may double as electrodes for collecting the ECG data. In another embodiment, a patch or surface of the CGM monitor or the insulin pump may double as the ECG electrodes. Such embodiments are depicted in FIG. 12. In an embodiment, an ECG electrode can be used for delivering and/or measuring insulin and/or glucose levels.

In an embodiment, bio-potential electrodes may be used for collecting ECG data. The bio-potential measurement, e.g., a voltage produced by a tissue of the body (e.g., a muscle tissue during a contraction) may be performed with conductive or non-conductive electrodes. Advantageously, non-conductive electrodes or capacitive electrodes do not need direct contact between skin and electrodes, thereby saving the time needed to expose and prepare the contact area when measuring with conductive electrodes. Non-conductive electrodes, however, may be more sensitive to effects of motion than conductive electrodes.

Bio-potential electrodes may consist of multiple layers of metal. For example, a first layer may be optimized to bond the housing of the artificial pancreas system (e.g. Cu on ABS plastic), a second layer may be primer electrode material (e.g., silver), and a third layer may be an optimization of the electrode material for improving the impedance matching between electrodes and the measuring objectives. In an embodiment with a silver primer electrode, the electrode may comprise silver-silver chloride (Ag/AgCl). In one embodiment the first binding layer may not be present. In one embodiment the third layer may be a disposable tape.

In various embodiments, the bio-potential-electrodes can be incorporated or embodied into any material like metal or foam material such as rubber, textile, or plastic. For optimized performance and electrical properties of electrodes it may be advantageous to add noble colloidal metal (e.g. silver, gold or platinum) particles suspended in a liquid directly to the bio-potential electrodes, or into the conducting gel, or by applying it directly to the skin of the subject before examinations. In such embodiments, the colloidal metal may improve the signal/noise ratio by reducing the skin impedance. Dry and/or old skin creates high impedance which makes it difficult to acquire good readings. The use of colloidal metal may eliminate the need for preparation of the patients' skin by lowering skin impedance.

In one embodiment the colloidal metal or other conducting material like chloride gel or a combination with colloidal and chloride may also be added to the adhesive patch from the CGM and insulin pump as depicted in FIG. 12.

The surface coated bio-potential electrodes in combination with the use of colloidal metal are not limited to ECG electrodes described herein, and many other applications of biological electrode systems such as biomonitoring electroencephalography (EEG), and Electromyography (EMG) may use such electrodes.

In one embodiment the glucose monitor, the ECG monitor, and the insulin pump may by combined with one or more of the wearable's sensors, shown in table 2, such as motions, breathing, EMG or EEG sensors.

The foregoing detailed description has set forth various embodiments of the devices and/or processes by the use of diagrams, flowcharts, and/or examples. Insofar as such diagrams, flowcharts, and/or examples contain one or more functions and/or operations, it will be understood by those within the art that each function and/or operation within such diagrams, flowcharts, or examples can be implemented, individually and/or collectively, by a wide range of hardware, software, firmware, or virtually any combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

All references, including but not limited to patents, patent applications, and non-patent literature are hereby incorporated by reference herein in their entirety.

Embodiments illustrating the devices, methods and systems described herein may be further understood by reference to the following non-limiting examples:

Examples

Detection of Hypoglycemia Based on Heart Rate Variability and CGM Data

Embodiments described in the examples may utilize the devices, methods and processes described herein with respect FIGS. 3-5.

Data Collection:

Data from 10 patients was obtained. 10 adults with type I diabetes were recruited for studies into hypoglycemia under clinical settings. None of the patients with diabetes had a history of cardiovascular disease. None of the patients were taking drugs affecting the cardiovascular system, and all had normal electrocardiograms.

On the study day, hypoglycemia was induced by a single subcutaneous bolus of insulin aspart. Subjects were placed in a hospital bed with the back rest elevated to a comfortable position. Equipment for measuring the ECG (lead II) and a CGM device (Guardian RT, Minimed, Inc., Northridge, Calif.) producing a reading every 5 minutes were mounted and an intravenous cannula was placed in an antecubital vein in both forearms. Blood samples for measurements of insulin were taken at the beginning and end of a baseline period. Throughout the experiment, blood glucose measurements were obtained frequently from earlobe capillary blood.

Blood glucose readings were spline resampled with a rate of 5 minutes equivalent to each reading of the CGM device. The blood glucose readings were used as reference for periods/events with hypoglycemia and categorize events as (i) hypoglycemia—defined as the point of time of a blood sample closest to the value of 3 mmol/l glucose, and normoglycemia—defined as the point of time of a blood sample approximately 1 hour prior to the hypoglycemic event.

Once the HRV and blood glucose data is collected, all data processing was performed using custom analysis software developed in MATLAB R2011b (Mathworks, Natick, Mass.).

Preprocessing:

The ECG V5 signal was used for detection of peaks and calculation of RR-intervals. RR-intervals were divided in epochs of 5 minutes during the trial. RR-interval outliers from each epoch were replaced with the mean from that particular epoch. Outliers were defined as RR-intervals deviating 50% from previous data RR-interval or outside 3 standard deviations.

Epochs were analyzed using HRV analysis software (HRVAS) module and 103 measures ranging from time domain, Poincare, Nonlinear, time-frequency to frequency domain were derived from the epoch. Two different models were used to estimate power spectra density: welch and auto regression.

Feature Extraction and Reduction:

In short, feature extraction and reduction is performed to find preferably small number of features that are particularly distinguishing or informative for the classification. Measures derived from RR-interval epochs 10-40 prior to an event were used for calculating multiple features. Table 2 shows calculations used to combine different epoch measures.

TABLE 2

List of equations used to combine HRV measures into features.

| Description | Equation |
|---|---|
| Differentiation | $M_y epc_{x1} - M_y epc_{x2}$ |
| Averaging | $\mu (M_y epc_{x1} \ldots M_y epc_{xn})$ |
| Slope | $\alpha (M_y epc_{x1} \ldots M_y epc_{xn})$ |
| Standard deviation | $\sigma (M_y epc_{x1} \ldots M_y epc_{xn})$ |
| Skewness | $Y_1 (M_y epc_{x1} \ldots M_y epc_{xn})$ |
| Ratio | $M_y epc_{x1} / M_y epc_{x2}$ |

$M_y$ represent a HRV measure y, $epc_{x1}$ represent an 5 minutes RR-interval epoch, $\mu$ is the arithmetic mean, $\alpha$ is the slope regression coefficients, $\sigma$ is the standard deviation, Y1 is the third standardized moment.

Example of features could be (a) the median heart rate averaged from epochs 10-20 prior to an event or (b) the skewness of standard deviation of Normal-to-Normal intervals (SDNN) from epochs 10-40 prior to an event.

To classify the patterns, 3296 different features were evaluated for their discrimination abilities. A ranking algorithm based upon a t-test was used to eliminate features. The ranking algorithm calculates an average separability criterion for each feature, which is the ability to separate the means of the two classes in relation to the variance of each class. The features are then correlated, and the feature with the lowest separability criteria is eliminated if correlation with higher ranking features exceeds the threshold. In this study a correlation threshold of 0.7 was used. To ensure that the features obtained would not be over fitted, i.e. to reach a low generalization error, a cross-validation method was used. A total of the best 20 features were used to inclusion in the classification model.

Classification Model:

Non-probabilistic binary linear classifier Support vector machines (SVM) was used to classify the events of normoglycemia and the events of hypoglycemia. First a forward selection method was used to select a subset of features for the optimal classification model. This selection was done including a cross-validation with ten groups, leaving 2 events out for classification and 18 events for training. Forward selection starts with no features and assesses every single feature and finds the best feature. This feature is then included as part of the optimal feature subset. All other features are added again to form a two-feature subset etc. this is repeated until new features doesn't increase the performance.

A subset of features selected is then used for the final classification model, which also included a ten-fold cross-validation. Sensitivity and specificity is used to evaluate the classification model.

Figure 6:
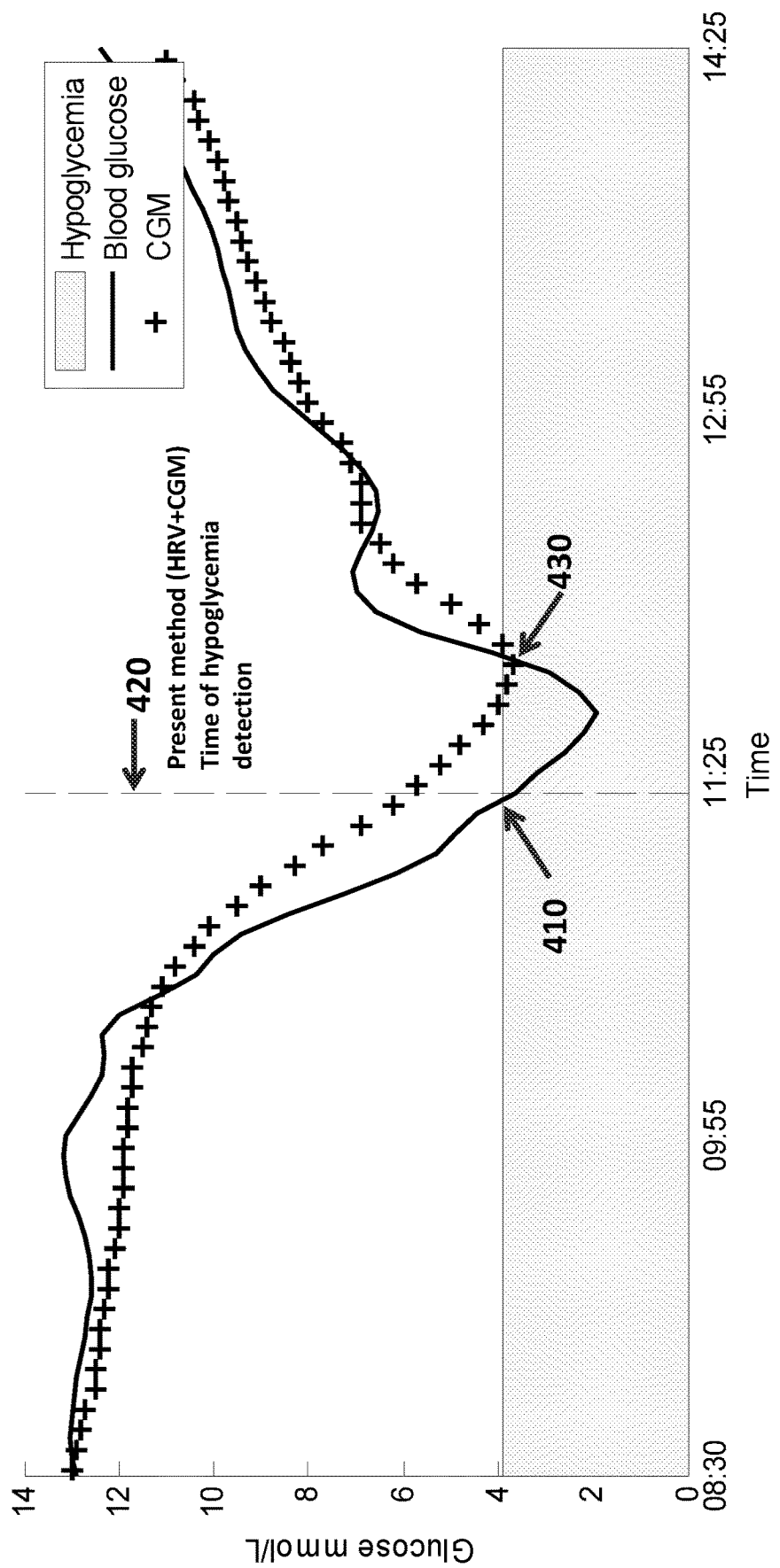
FIG. 6 shows an example of detection of hypoglycemia based on HRV data and data from a Continuous Glucose Monitor (CGM) for a subject, in accordance with the principles and aspects of the present disclosure.

Results:

A total of 903 samples equivalent to 4515 minutes among 10 patients with 16 hypoglycemic events were analyzed and classified using the model. The sample-based evaluation yielded a ROC AUC of 0.98. With a specificity of 99% the model had a sensitivity of 79%. This is a significant improvement over CGM alone. Event-based, the model classified all hypoglycemic events correctly, did not detect any false-positive events and had a lead-time of 22±(12) minutes. CGM alone was able to detect 12 out of 16 events with a lead-time 0±(11) minutes. FIG. 6 shows the data for one patient where CGM alone detects hypoglycemia, indicated by 430, late after the real onset, indicated by 410, while the present method detects the hypoglycemic event, indicated by 420, one minute after the real onset.

Example 2: Prediction and Improved Detection of Spontaneous Hypoglycemic Events

Methods

Participants: A total of 21 (13 men and 8 women) adults with long lasting T1D were recruited. The patients were 58±10 years old, had a diabetes duration of 34±12 years and a HbA1c 7.9±0.7%, and 11 participants had peripheral neuropathy measured by biothesiometer. All participants were prone to hypoglycemia, i.e. they had experienced at least two episodes of severe hypoglycemia within the last year. None of the patients had a history of cardiovascular disease or were taking drugs affecting the cardiovascular system. All patients had a normal electrocardiogram. The study protocols were approved by the local ethics committee and the study conducted according to the principles of the "Helsinki Declaration II". All patients gave their written informed consent.

Study Design: ECG was measured from lead II using a digital Holter monitor (SpiderView Plus; ELA Medical, Montrouge, France). At the same time, CGM was monitored using a Guardian Real-Time Continuous Glucose Monitoring System (Medtronic MiniMed, Northridge, Calif., USA) with the prevailing glucose level blinded. At 11 PM a cannula was placed into an antecubital arm vein. Blood glucose samples were taken at hourly intervals until 7 AM the next morning. At 8 AM, participants were sent home with the monitoring equipment and they were instructed to calibrate the CGM at least four times a day. Monitoring ended on Sunday at 8 PM. A total of 72 hours of continuous CGM and ECG data were available for each participant.

Data Processing: The ECG was analyzed using custom analysis software developed in MatLab (Version R2014a; MathWorks, Natick, Mass., USA). ECG QRS detection was implemented based on the methods of Pan and Tompkins with (a) bandpass filter, (b) differentiating, (c) squaring and (d) moving-window integration (19). Initial R-peaks were identified with a threshold and a minimum time distance of 250 ms from the moving-window integration output. R detections were then found as the highest point in the original signal within the timeframe of the initial detected peak. Inter-beat intervals were derived from the R detections and interpolation was used to remove outliers based on 2·StdHRV. The filtered HRV signal was inspected manually and periods with substantial noisy signals were labeled for excluding glucose measurements with appertaining corrupted HRV. The HRV signal was analyzed with a five min, 90% overlapping sliding window calculating typical derived measures describing HRV; heart rate, SDNN (Standard deviation of all NN intervals), SDANN (Standard deviation of the averages of NN intervals in all 5 min segments of the entire recording), pNNx (Proportion of pairs of adjacent NN intervals differing by more than 50 ms), RMSSD (The square root of the mean of the sum of the squares of differences between adjacent NN intervals), VLF (Power in very low frequency range, <0.04 Hz), LF (Power in low frequency range, 0.04-0.15 Hz), HF (Power in high frequency range, 0.15-0.4 Hz), TP (total power of all frequencies), LF/HF (ratio of LF and HF), entropy.

Figure 13:
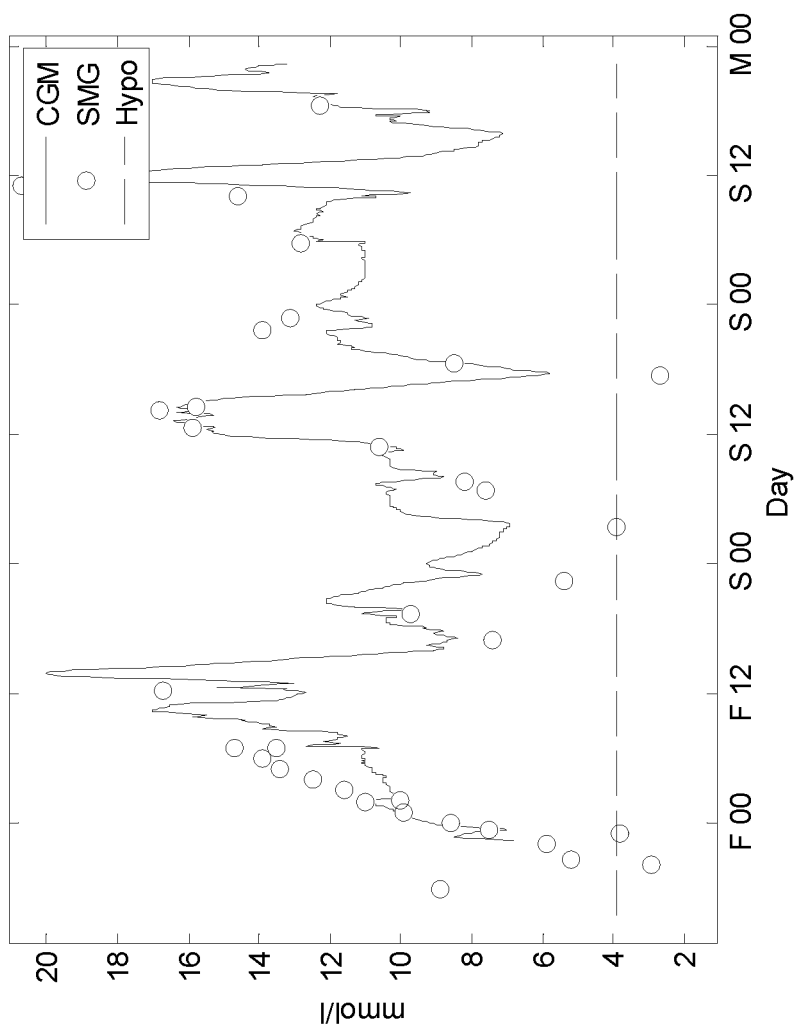
FIG. 13 depicts a graph of continuous glucose measurements and periodic single glucose measurements obtained from one subject.

The CGM signal was spline resampled to remove short periods with dropouts. Dropouts defined as periods with no measurements shorter than 15 minutes. Single measurement of glucose (SMG), such as blood plasma glucose or self-monitoring of blood glucose levels below 3.9 mmol/L (70 mg/dL) were labeled as a hypoglycemic event and otherwise as euglycemia. Glucose spot measurements with corresponding CGM readings showing a discrepancy of 8 mmol/L (144 mg/dl) or more were considered as erroneous data in either the CGM or spot measurement and they were therefore excluded from further analysis. Furthermore, spot measurements within two hours after a hypoglycemic event were excluded since such an event may affect the heart rate during the recovery phase. FIG. 13 shows CGM readings with corresponding SMG readings from one participant. The dashed line illustrates the threshold for labeling SMG reading as either hypoglycemic or euglycemic.

Figure 14:
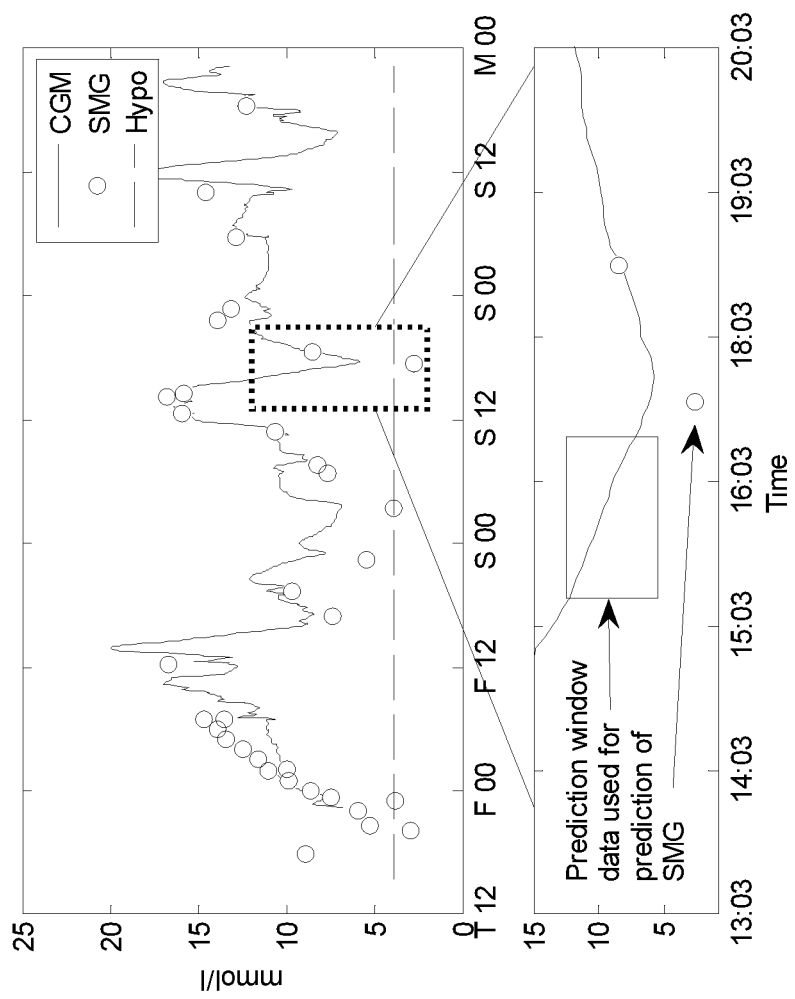
FIG. 14 depicts a time window used for predicting a single glucose measurement using continuous glucose measurements and heart variability data.

Pattern Classification: We developed a pattern classification method to predict single measurements of glucose (SMG) into one of the two classes: being within the range of hypoglycemia, or euglycemia. The method was based on extracting features from the CGM signal and the derived HRV signal prior to the SMG. A classification model was applied, using features that produced the best prediction model. The approach is illustrated in FIG. 14, where data in a 60 min prediction window 10 min prior to the SMG has been used to extract features for prediction. In short, we used different time intervals within the prediction window to calculate several derived features from the CGM and the corresponding HRV signals. The nature of this approach results in a large number of features. To eliminate uninformative features, we used a ranking and correlative method where the receiver operating characteristic (ROC) for every feature was calculated. The result was weighted based on the correlation with higher-ranking features. The 40 most informative features were kept and the rest were discarded. To find a subset of the most informative features for model inclusion, we used forward selection and concurrently a 10-fold cross validation. The model used for classifying the patterns was based on logistic regression classification.

Performance: For evaluation of the hypothesis that HRV could add information in the prediction of hypoglycemia, we assessed and compared three different models; (i) one model (CGM) containing only the raw information from the CGM; (ii) one model (CGM*) containing features derived from the CGM signal in the prediction window and (iii) one model (CGM+HRV) containing both features derived from CGM and HRV. The classification performance was evaluated by sample-based sensitivity and specificity along with ROC and absolute number of true positives, true negatives, false positives and false negatives for a chosen best model. Each SMG reading was predicted as either hypoglycemic or euglycemic, and the truth of each classification was calculated subsequently. Calculation of the different model (i-iii) performances was based on the prediction window starting 0-30 min prior to the SMG readings. Hence, a prediction window starting 30 min prior to the reading will yield a 30-min prediction interval.

Results

Figure 15:
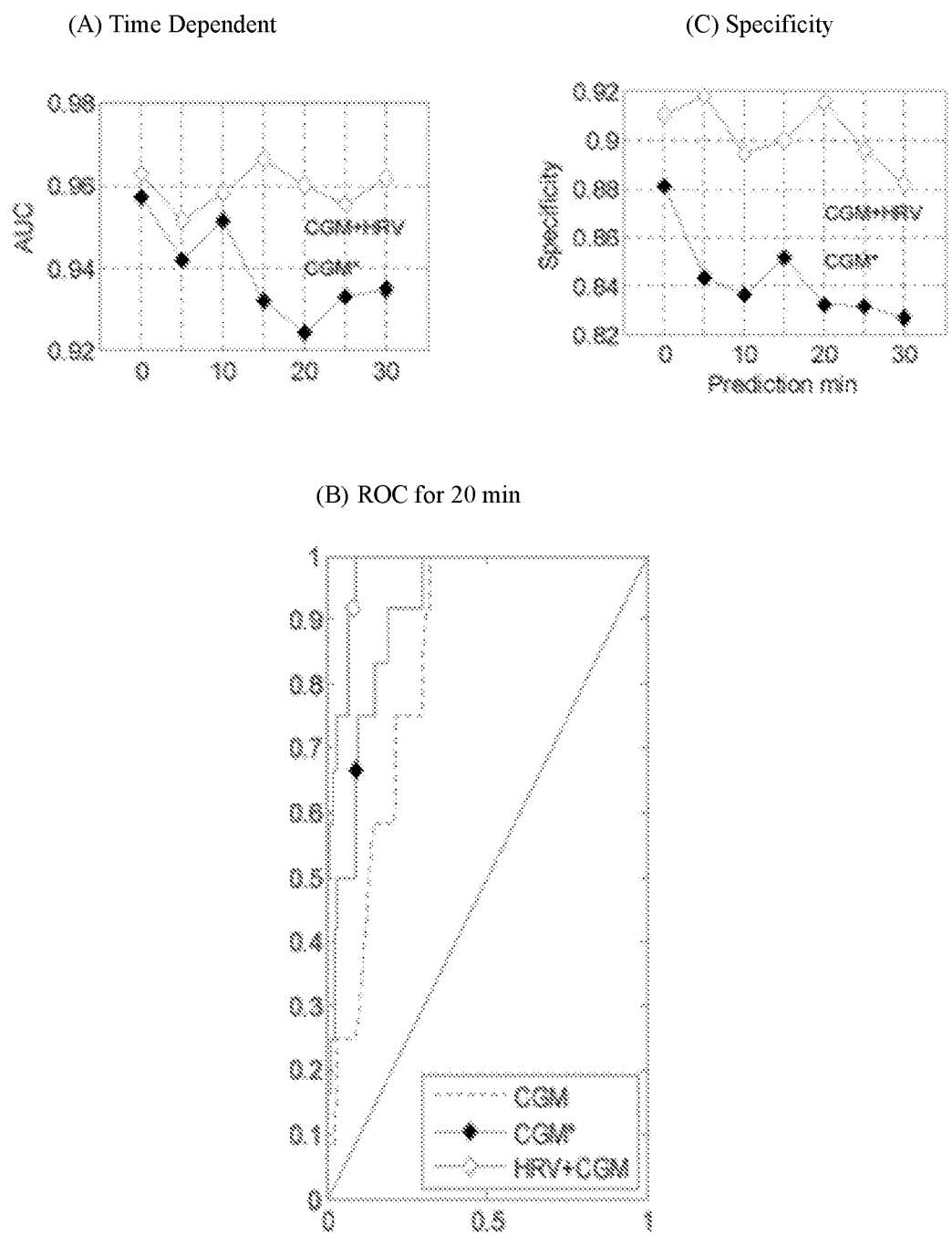
FIGS. 15A-15C depict comparison of various parameters for models using glucose only and glucose in conjunction with heart rate data for prediction of hypoglycemic events.
Figure 16A:
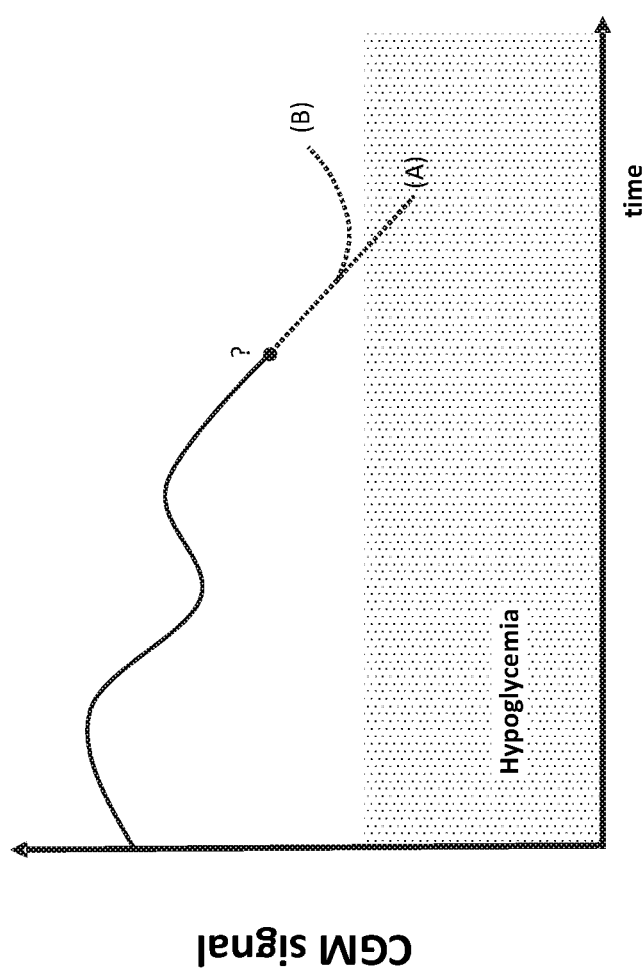
Figure 16C:
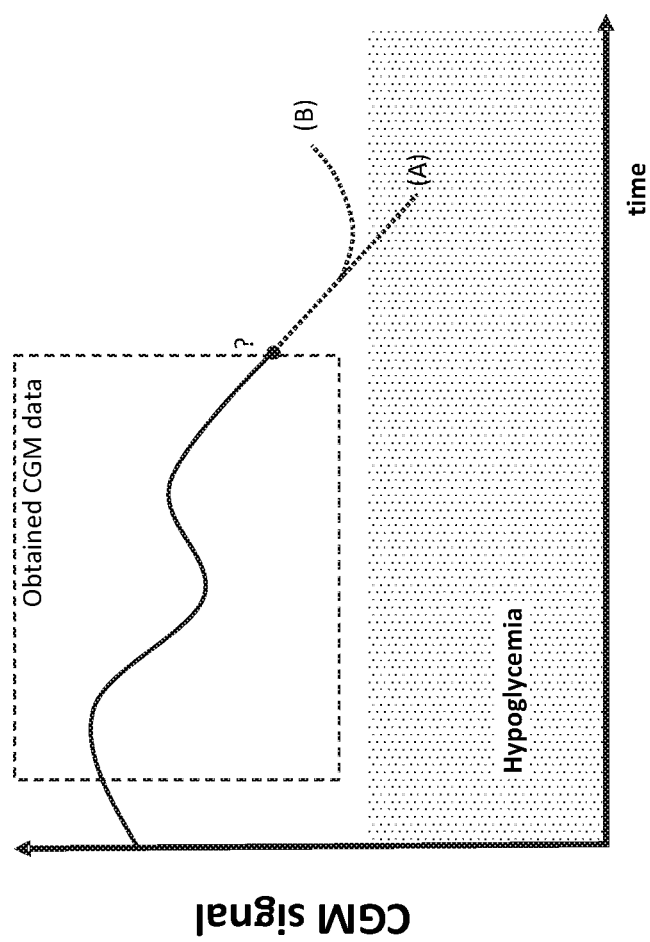
Figure 16D:
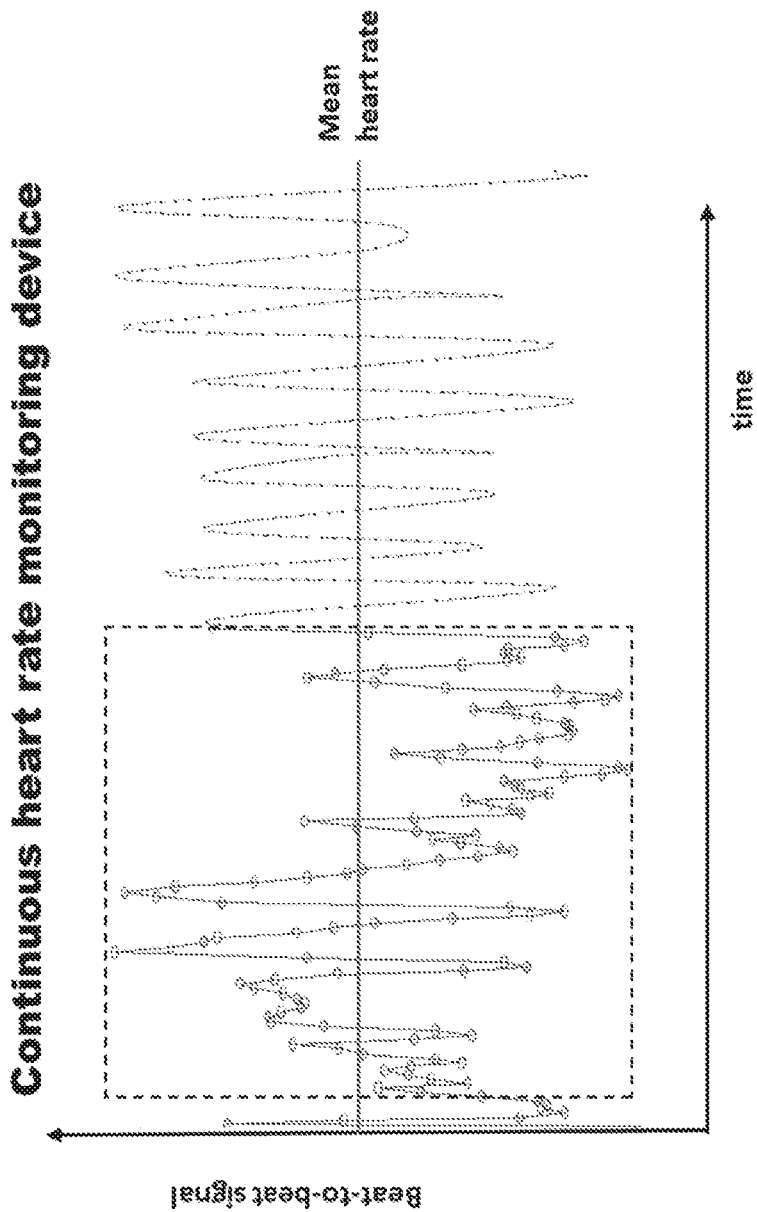
Figure 16E:
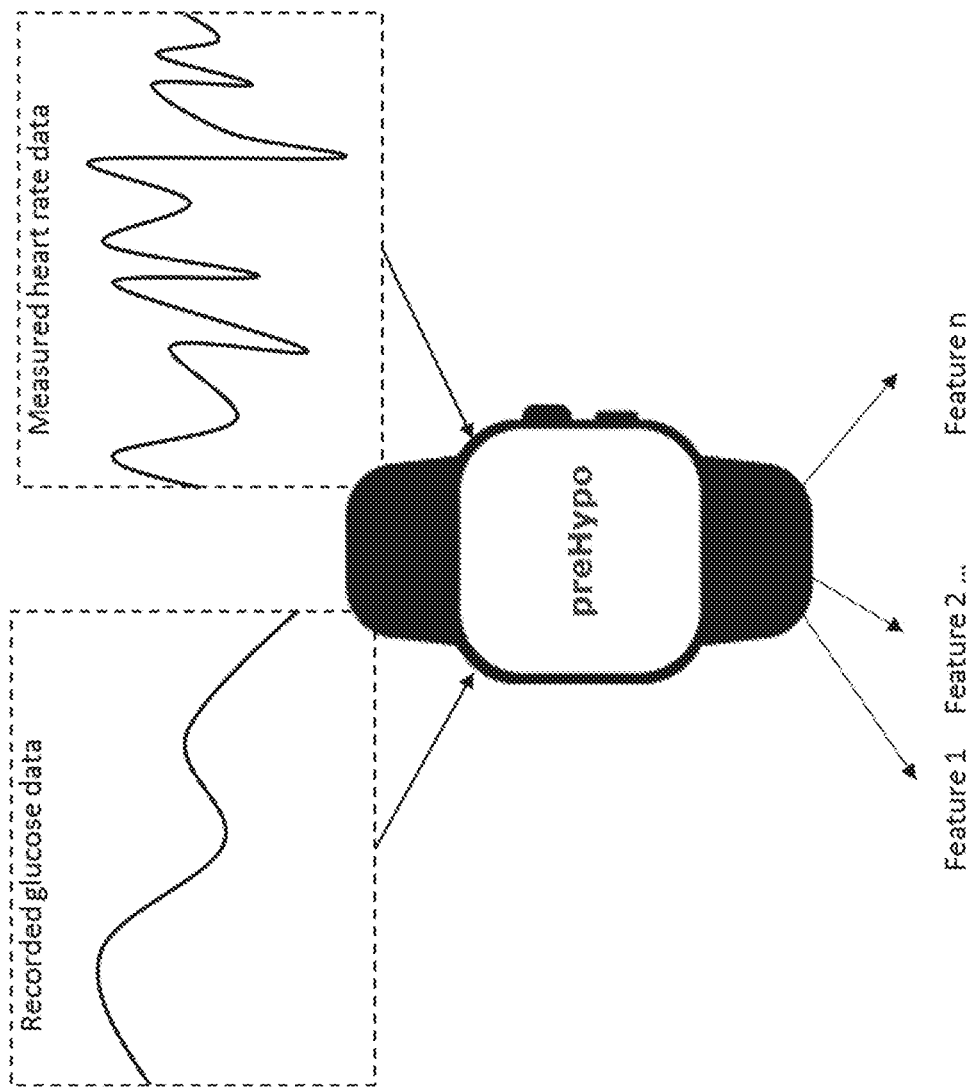
Figure 16F:
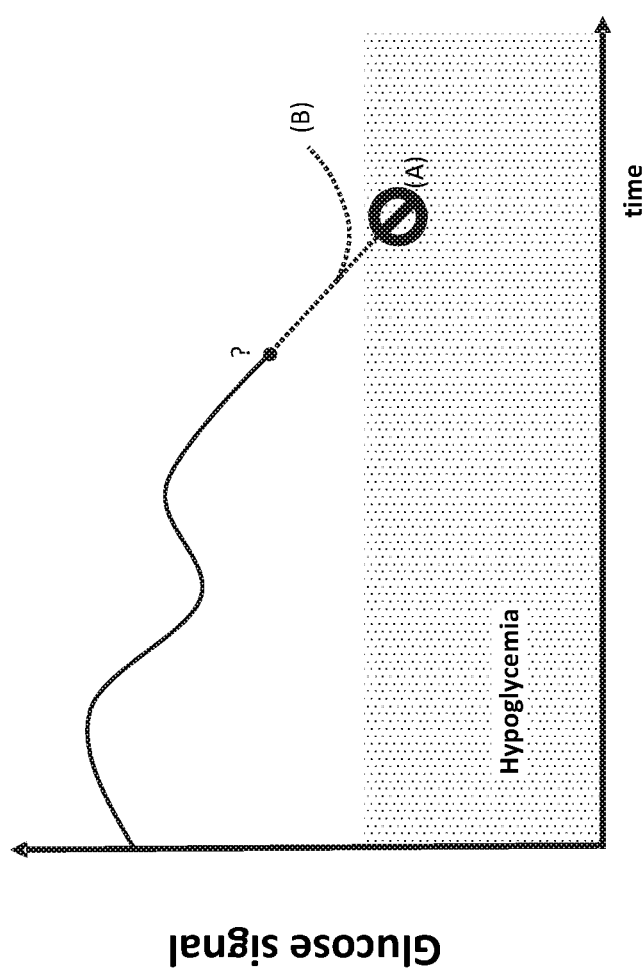

A total of 12 hypoglycemic events and 237 euglycemic SMG readings were included in the 21 datasets. For a 20 min prediction of the SMG reading the: (i) CGM model had a ROC AUC of 0.69 with a corresponding sensitivity of 100% and a specificity of 69%. The CGM* model (ii) yielded a ROC AUC of 0.92 with a corresponding sensitivity of 100% and specificity of 71%. (iii) The CGM+HRV model yielded a ROC AUC of 0.96 with a corresponding sensitivity of 100% and specificity of 91%. The relative and absolute numbers for the 20 min prediction are seen in Table 3 and the corresponding ROC for the three models are depicted in FIG. 15, which shows the comparison of the (ii) CGM* model and the (iii) CGM+HRV model with varying prediction times. FIG. 15 shows the performance (ROC AUC and Specificity) of the models ii and iii as a function of prediction time. Such that a prediction of 30 min will give, a 30 min forecast. The CGM+HRV model is obtaining a higher specificity when sliding prediction time from 0 to 30 min, whereas the CGM* model is steadily losing prediction power. The difference between the models in the time dependent analysis is significant ($p<0.05$).

TABLE 3

| MODEL | SEN | SPE | AUC | TP | TN | FP | FN |
| --- | --- | --- | --- | --- | --- | --- | --- |
| (I) CGM | 100% | 68% | 69% | 12 | 161 | 76 | 0 |
| (II) CGM* | 100% | 71% | 92% | 12 | 168 | 69 | 0 |
| (III) CGM HRV | 100% | 91% | 96% | 12 | 216 | 21 | 0 |

Performance represented as sensitivity (SEN), specificity (SPE), area under curve (AUC), true positive (TP), true negative (TN), false positive (FP) and false negative (FN)—with a prediction of 20 minues.
Performance compared between that of CGM (current reading), CGM* algorithm with features from the CGM and CGM + HRV algorithm with features from both CGM and HRV.

Example 3: Closed-Loop System During Daily Living

In the closed-loop system the insulin pump/CGM device controls when to dose with insulin and glucagon to prevent hypoglycemia. Using a closed-loop system as describing in this application at all time would be ideally, but may not be possible during daily living. Device safety issues during automated delivery of medication may be issue during daily living. CGM, Heart rate measurement device and insulin pump must work independently and as plug-and-play and connect automatically and securely with wireless body area network (or similar technology) every time the devices are in range of each other. Minor devices failures e.g. low battery in heart rate monitor, must not affect the improved detection of low blood glucose in CGM device. According to the result in Example 2 Table 3. The CGM* model (ii) yielded a ROC AUC of 0.92 with a corresponding sensitivity of 100% and specificity of 71%. (iii) The CGM+HRV model yielded a ROC AUC of 0.96 with a corresponding sensitivity of 100% and specificity of 91%.

Therefore, we developed a pattern classification method to predict single measurements of glucose (SMG) into one of the two classes: being within the range of hypoglycemia, or euglycemia. The method was based on extracting features from the CGM the pattern prior to the SMG. A classification model was applied, using features that produced the best prediction model. The approach is illustrated in FIG. 14, without HRV, where data in a 60 min prediction window 10 min prior to the SMG has been used to extract features for prediction. In short, we used different time intervals within the prediction window to calculate several derived features from the CGM signals. The nature of this approach results in a large number of features. To eliminate uninformative features, we used a ranking and correlative method where the receiver operating characteristic (ROC) for every feature was calculated. The result was weighted based on the correlation with higher-ranking features. The 40 most informative features were kept and the rest were discarded. To find a subset of the most informative features for model inclusion, we used forward selection and concurrently a 10-fold cross validation. The model used for classifying the patterns was based on logistic regression classification.

In order to achieve the maximum protection and the possibility to predict low blood glucose both the CGM and HR must be recorded in real-time and the algorithm will automatically use both measurements. However, if the heart rate measurement device is removed the algorithm will continue to work and only use the CGM measurements.

Case Story

Patient J is an active young person with type 1 diabetes. He uses a continuous glucose monitoring device (CGM) on a daily basis. As shown in FIG. 15A, today his glucose levels have been alternating—and at this point in time (T) his blood glucose has declined but is still within the normal range. Should Patient J do something to prevent additional decline or is the declining blood glucose within normal daily variations?

As shown in FIG. 15B, Patient J is lucky he uses a smart watch that enables continuous heart rate (HR) monitoring device. The CGM device, with the algorithm installed and HR data (HRV) are connecting automatically and securely with wireless body area networks (or similar technology) every time Patient J takes his watch on. In order to achieve the maximum protection and the possibility to predict low blood glucose both the CGM and HR are be recorded in real time. However, the CGM may also use the algorithm alone to just to detect low blood glucose. If there is an error in Patient J's watch e.g. low battery, then the algorithm will continue to operate and improve detection of low blood glucose in CGM device as shown in table 3 of the application.

As shown in FIG. 15C, already obtained CGM and HR data comprise information about the type of decline Patient J is experiencing. Therefore, as shown in FIG. 15D, Patient J has the tools to determine whether the blood glucose decline could lead to an episode of severe and potentially life threatening hypoglycemia.

As shown in FIG. 15E, the preHypo algorithm uses this historically obtained data from Patient J's CGM and HRV device to predict the glucose waveform. It is all done automatically by his smart-watch (and/or CGM device). The data is filtered and processed to obtain a sequence of mathematically derived features.

The patterns from Patient J's data resemble pattern from other data, which have led to a hypoglycemic episode. Therefore, Patient J's smart phone flags Patient J, alarming him that he should be cautious. This is done by triggering a customized and personalized alarm from Patient J's smart watch. Thereby enable Patient J to intervene by timely drinking or eating sugary fluids (juice) or food. As shown in FIG. 15F, after food intake the preHypo algorithm will detect the raising blood sugar and give a personalized feedback to Patient J.

If Patient J had used his closed-loop system all this had happened automatically without alarm or need for Patient J to intervene by timely drinking.

Point-of-Care Device

In an embodiment the point-of-care device disclosed herein may be combined with sensors and electronics so that the device is able to measure and control one or more of the sensors, shown in table 4, e.g. EMG or EEG sensors.

In an embodiment the sensor and measurement listed in table 4 are wearables and can be used in combination with the cardio reflex tests.

In an embodiment the point-of-care device disclosed herein may be combined with a CGM device and may be used for calibration of the Algorithm which is installed on CGM devices. Furthermore it enables CGM measurements in combination with cardioreflex tests.

Table 4 provides a list of measurements that may be used in concert with HRV calculated from ECG recordings.

TABLE 4

Examples of sensors/measurements that are link to autonomic nervous system

EEG-electroencephalogram
Nerve conduction
EMG-Electromyography
Sudomotor function-Bioimpedance measurement
Pulse wave velocity
Blood pressure
Breathing (sounds and rate)
Motion detection-accelerometer List of biomarkers or biomarker surrogates used for detection/prediction for physiological events/conditions (EEG-electroencephalogram; EMG-Electromyography; ECG-Electrocardiography).

Figure 17:
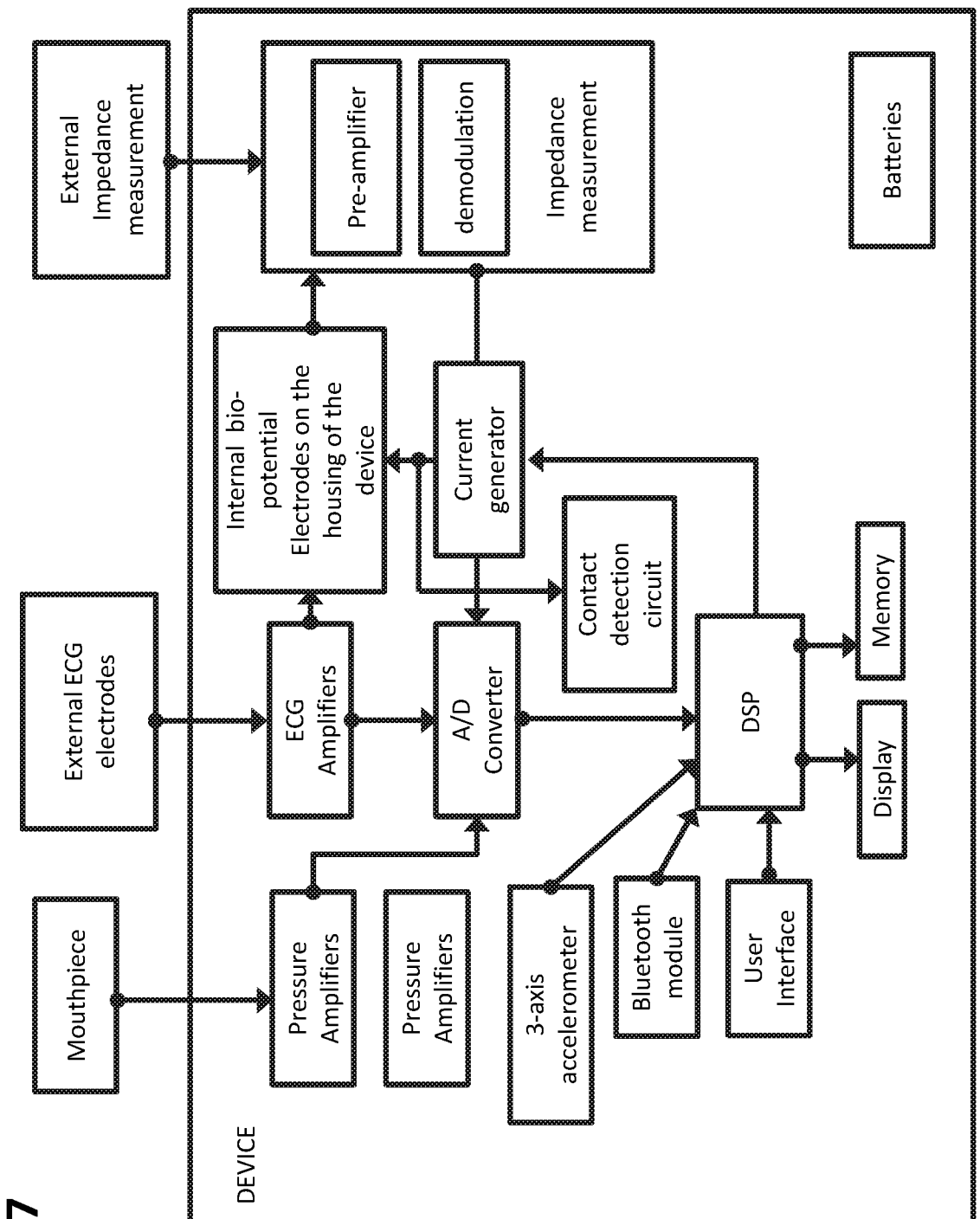
FIG. 17 show a block diagram for the point-of-care device.

FIG. 17 show a block diagram for the point-of-care device. The device has interchangeable and independent bio-electrodes forming a part of the housing of the device. These bio-electrodes can be used to measure bio-impedance or ECG from the hand for the person being examined. During impedance measurement an alternating current is supplied to the tissue through one or more of the electrodes. A modulated bio-impedance signal is recorded using one or more separated electrodes. The pulse wave signal is demodulated, sampled, and processed further in a digital signal processor (DSP). The signal from the current-generator is fed back to a contact-detection circuit that, based on the amplitude of the voltage needed to supply the alternating current, can detect if the electrodes have poor contact and signal this to the operator via the DSP and the display. External bio-electrodes may be connected to the device for impedance plethysmography measuring and for up to 12-Lead ECG measurement. External sensors that are shown in table 1 may be connected with the device via Bluetooth, wireless body sensor networks or similar technology.

Oscillometric blood pressure measurements using cuffs are inappropriate in the tests of autonomic nervous system. The main goal with autonomic cardioreflex tests is to measure a sudden change in blood pressure in response to external stimuli (e.g. form laying to standing, deep breathing, forced expiration). During the Valsalva maneuver the patient forcefully exhale for only 15 seconds through a mouthpiece and breathe normally hereafter for 45 seconds. During the test from laying to standing form a transient decrease in blood pressure and increase in heart rate due to translocation of blood from the central intravascular compartment to the veins. The translocation of blood reduces venous return to the heart, and consequently further induces stroke volume and cardiac output. This activates the arterial baroreceptors with an increase in heart rate and total peripheral resistance. In healthy subjects, the heart rate and blood pressure reach normal homeostatic levels after approximately 30 seconds. During deep breathing, inspiration causes a reduction in intrathoracic and abdominal pressure which increases venous return to the heart (preload) resulting in increased stroke volume and heart rate. During expiration, venous return to the heart is reduced due to a reduction of intrathoracic and abdominal pressure. This decreases cardiac preload and results in decreased stroke volume and heart rate. The above described tests are perform during 1 minute each and the slow and discomfort cuff measurement is therefore an inappropriate measuring technique and may stress the patient unnecessary during the cardiovascular reflex tests.

Changes in blood pressure may be measured continuously using the pulse wave signals derived from photo or impedance plethysmography recordings. These measuring techniques can be built-in a watch (smart-watch), Velcro band or attach to the patient with an adhesive substance.

In an embodiment the pulse wave signal is measured by the measurable change in electrical impedance when the pulse wave moves though the arteries. Impedance plethysmography includes the use of two or more bio-potential electrodes, platinum electrodes, which are attached to the skin surface around the measuring object. The electrodes may afterwards are be connected with wires or wireless to the actual measuring apparatus.

In an embodiment two or more impedance or photo plethysmography sensors are attached to e.g. the arm for the patient with a known distance between the two points of measurement which enables the measurement of pulse wave and pulse wave velocity in combination with the cardioreflex tests.

In an embodiment detailed analysis of the pulse wave may be performed using one or more of analysis tools such as, of in various embodiments, include, for example, differentiation, averaging, calculation of slope, ratios of instantaneous values, standard deviation, skewness, regression coefficients, slopes of regression ratios, and standardized moment, area under the curve, Poincare Plots, Nonlinear analysis, time-frequency analysis and performed in time domain or frequency domain. Power spectra density may then be estimated using parametric or non-parametric models such as, for example, Welch's method, auto regression, periodogram, Bartlett's method, autoregressive moving average, maximum entropy, least-squares spectral analysis, and so forth.

In an embodiment impedance or photo plethysmography sensors are combined with 3-Axis accelerometer at each measuring point to record and remove movement artifacts from the signal for interest.

By combining real-time blood pressure measurement and ECG measurement. It possible to measure the so-called baroreflex sensitivity (BRS). BRS is a measure of heart and cardiovascular autonomic reflection/Pressure-buffer system, which main task is to regulate and keep blood pressure within narrow limits.

BRS is a direct measurement of the Pressure-buffer system and is defined as the change in R-R interval in the ECG due to change in systolic blood pressure and measured in [ms/mm Hg]. A BRS value of 10 ms/mmHg thus means that systolic blood pressure is increased by 1 mmHg, at an extension of the RR interval of 10 ms. In young healthy individuals is baroreflex sensitivity between 15-20 ms/mmHg.

FIGS. 18A-18B show an example for the handheld point-of-care device. FIG. 18A shows the intact device and B shows the device after removal of cover 1803 and the round bio-electrodes 1801. The bio-electrodes are connected to the electronics with the connectors 1804. The user interface includes buttons 1806 and the display 1802. The tube of external mouthpiece is connected to tab 1805.

In an embodiment, bio-potential electrodes may be used for collecting ECG data. The bio-potential measurements, e.g., a voltage produced by a tissue of the body (e.g., a muscle tissue during a contraction) may be performed with conductive or non-conductive electrodes. Advantageously, non-conductive electrodes or capacitive electrodes do not need direct contact between skin and electrodes, thereby saving the time needed to expose and prepare the contact area when measuring with conductive electrodes. Non-conductive electrodes, however, may be more sensitive to effects of motion than conductive electrodes.

Bio-potential electrodes may consist of multiple layers of metal. For example, a first layer may be optimized to bond the housing of the device (e.g. Cu on ABS plastic), a second layer may be primer electrode material (e.g., silver), and a third layer may be an optimization of the electrode material for improving the impedance matching between electrodes and the measuring objectives. In an embodiment with a silver primer electrode, the electrode may comprise silver-silver chloride (Ag/AgCl). In one embodiment the first binding layer may not be present. In one embodiment the third layer may be a disposable tape.

In various embodiments, the bio-potential-electrodes can be incorporated or embodied into any material like metal or foam material such as rubber, textile, or plastic. For optimized performance of the electrical properties of electrodes it may be advantageous to add noble colloidal metal (e.g. silver, gold or platinum) particles suspended in a liquid directly to the bio-potential electrodes, or into the conducting gel, or by applying it directly to the skin of the subject before examinations. In such embodiments, the colloidal metal may improve the signal/noise ratio by reducing the skin impedance. Dry and/or old skin creates high impedance which makes it difficult to acquire good readings. The use of colloidal metal may eliminate the need for preparation of the patients' skin by lowering skin impedance.

In one embodiment the colloidal metal or other conducting material like chloride gel or a combination with colloidal and chloride may also be added to the adhesive patch from standard ECG electrode.

In one embodiment the bio-potential electrodes is an integral part of the apparatus and thus has given great freedom of design. This is achieved according to the present invention with the use of surface coating technology like PVD (Physical Vapor Deposition) coating.

The surface coated bio-potential electrodes in combination with the use of colloidal metal is not limited to ECG electrodes described herein, and many other applications of biological electrode systems such as biomonitoring of impedance plethysmography, electroencephalography (EEG), and Electromyography (EMG) may use such electrodes. Furthermore, the bio-potential electrodes may be integrated into exercise equipment or controllers for e.g. game consoles.

Figure 18E:
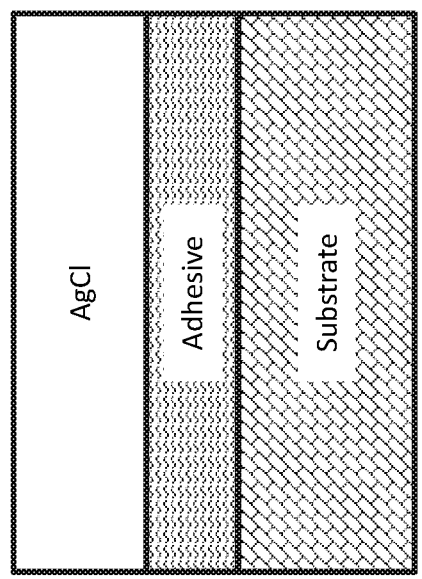

FIGS. 18C-18E show details of the electrode 1801. The electrode 1801 has at least two sub-electrodes 1811 and 1813. The sub-electrodes 1811 and 1813 are separately addressable. The sub-electrodes 1811 and 1813 may be electrically separated by an insulating portion 1812. The electrode 1801 may have electrical contacts 1814 for electrically connecting the sub-electrodes 1811 and 1813 to the rest of the point-of-care device. In the example shown in FIGS. 18C-18E, the sub-electrodes 1811 and 1813 may include electrically conductive films on an electrically insulating substrate (e.g., plastic). The insulating portion 1812 may be a portion of the substrate not coated with an electrically conductive film. The sub-electrodes 1811 and 1813 may include partial cylindrical films. As shown in FIG. 18E, the sub-electrodes 1811 and 1813 may be a film of AgCl supported on the substrate with an adhesive in between. The adhesive is for attaching the film of AgCl to the substrate. An example of the adhesive is a layer of copper. The film of AgCl may be made by depositing a film of Ag and chlorinating the film of Ag. It is possible that a layer of unchlorinated Ag exists under the film of AgCl. The electrode 1801 may be disposable.

Figure 19:
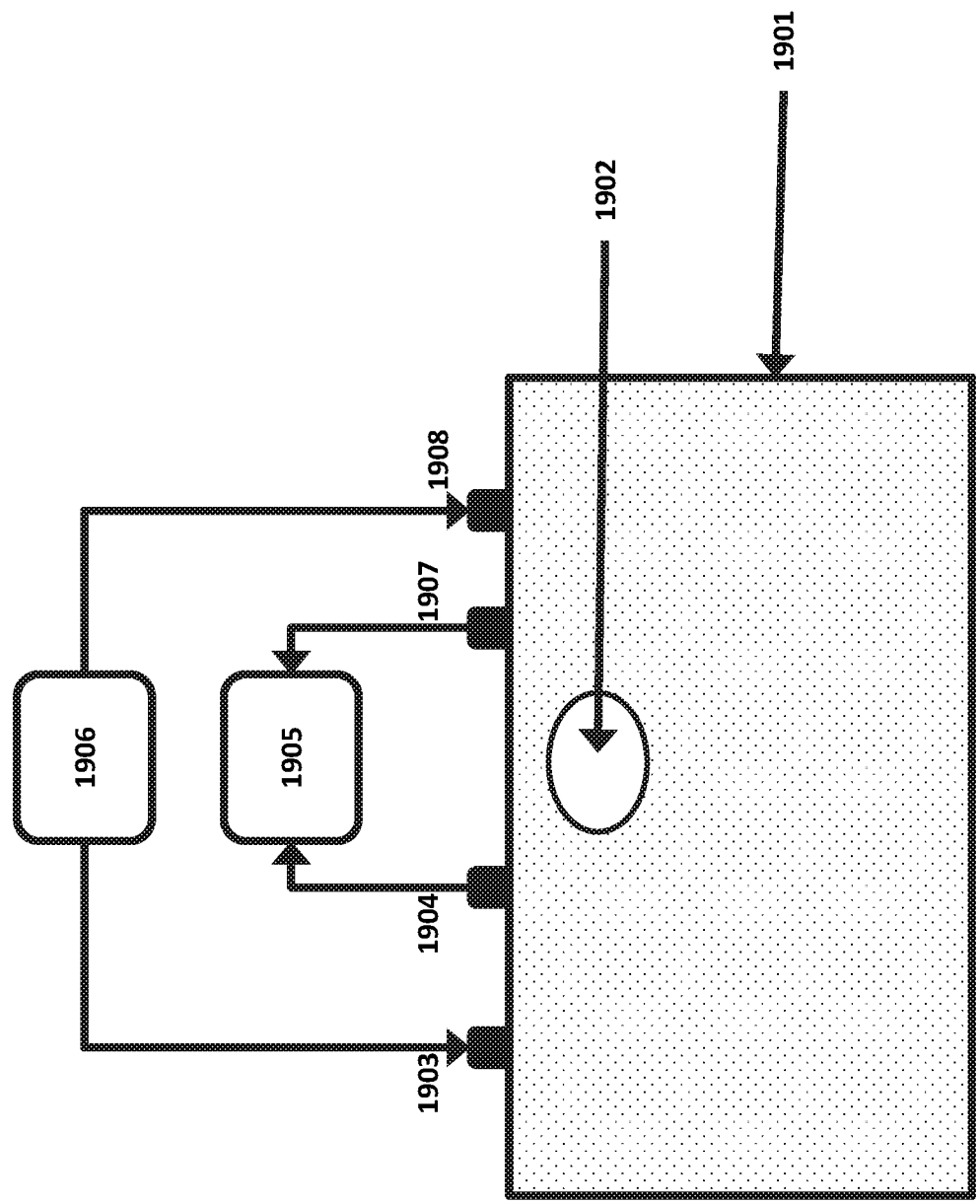
FIG. 19 shows an elementary sketch of a measurement of impedance for measurement of pulse wave.

The sub-electrodes of the two electrodes 1801 collectively can measure impedance. FIG. 19 shows an elementary sketch of a measurement of impedance for measurement of pulse wave. In FIG. 19, 1901 indicates a cross section of a measured object, e.g., in form of a segment of a human forearm, and 1902 show a superficial artery. On the surface of the object of measurement, which, in the example, is the surface of the person's skin, sub-electrodes 1903, 1904, 1907 and 1908 are placed. The sub-electrodes 1904 and 1907 are connected to a signal detection circuit 1905, while sub-electrodes 1903 and 1908 are connected to a signal generation circuit 1906. In practice, the signal generation circuit 1906 is a source of electrical current, where alternating current is preferred, while the signal detection circuit is a voltage detector. During a measurement, the signal, being the alternating current, which from 1906 is penetrating the measured object 1901, as well as the resulting voltage, which is registered in the detection circuit 5 is known. With knowledge of the current through, as well as the voltage across the object of measurement the impedance can simply be derived based on the formula R=V/I, where R is the impedance in the volume of measurement, which is covered by the measurement setup, V is the voltage, which is measured in 1905 and I is the current, which is generated from 1906. In the electrode 1801 shown in FIGS. 18C-18E, each hand of the patient touches both sub-electrodes of the electrode 1801 when the patient holds the device.

The cubical content, which is defined by the measuring set-up, is primarily dependent of the mutual location of the electrodes and their physical extent. As the volume of blood in the superficial artery under the electrodes changes due to the pulse wave, the average impedance detected by the two medial electrodes also change. Because the blood, which flows through the artery, has a characteristic impedance different than the nearby tissue, the pulse wave in the artery can be registered in the signal detector 1905.

Disposable Respiratory Device for Cardioreflex Tests

Figure 20:
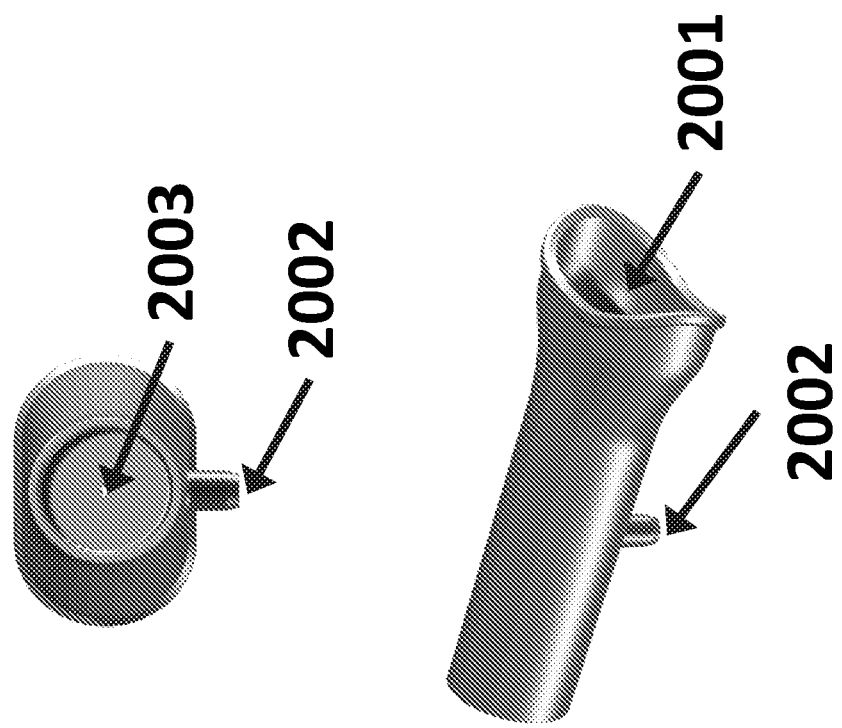
FIG. 20 shows an example of the mouthpiece.

FIG. 20 shows an example of the mouthpiece. In FIG. 20, 2001 is the air inlet for receiving expired air from a patient. The air inlet is connected to an interior cavity. The tube is connected to the mouthpiece via a first air outlet 2002 and pressurized air are guided from the first air outlet to a pressure sensor of said the device and described in FIG. 19. The mouthpiece also has an air leak 2003 for building up pressure in the interior cavity. The mouthpiece may have a second air outlet 2005 that may be blocked by a movable part, which makes it possible to perform both the Valsalva maneuver or deep breathing test with the same mouthpiece.

The mouthpiece may be operated by the patient without using his/her hands. Thus, the patient may operate the mouthpiece while his/her hands are positioned on for example a pair of ECG electrodes.

The mouthpiece may be connected to an associated medical device in that pressurized air should be guided from the first air outlet to a pressure sensor of said other medical device. Said medical device may further comprise ECG electrodes so as to facilitate simultaneous measurements of exhale pressure and heart beat. Such simultaneous measurements are essential when carrying out a Valsalva maneuver or deep breathing tests.

When the movable is positioned to block the second air outlet for the Valsalva maneuver, the air leak 2003 can help to avoid closure of the glottis.

The mouthpiece may further comprise a guide for guiding the moveable part from the second air outlet to the interior cavity of the first air outlet in response to the patient's inhalation of air through at least part the disposable respiratory device. The guiding means may provide on an interior surface portion of a housing of the mouthpiece, preferably forming an integral part of the interior surface portion of a housing of the mouthpiece. The housing of the mouthpiece may comprise an injection mouldable material, such as an injection mouldable polymer material.

The moveable part may comprise a substantially spherical element, preferably comprising an injection mouldable material, such as an injection mouldable polymer material.

Figure 21:
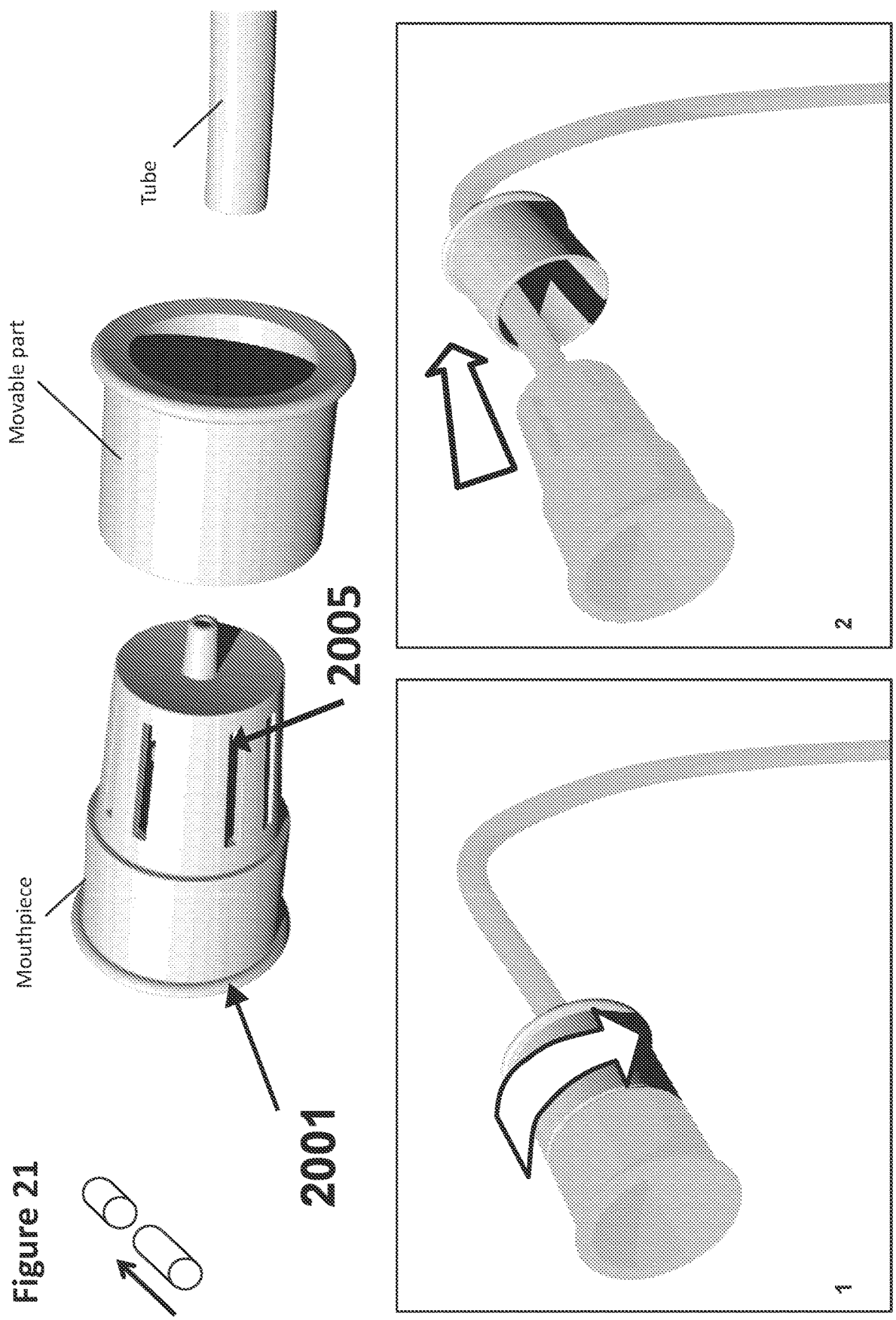
FIGS. 21 to 23 shows different designs of the mouthpiece.
Figure 22:
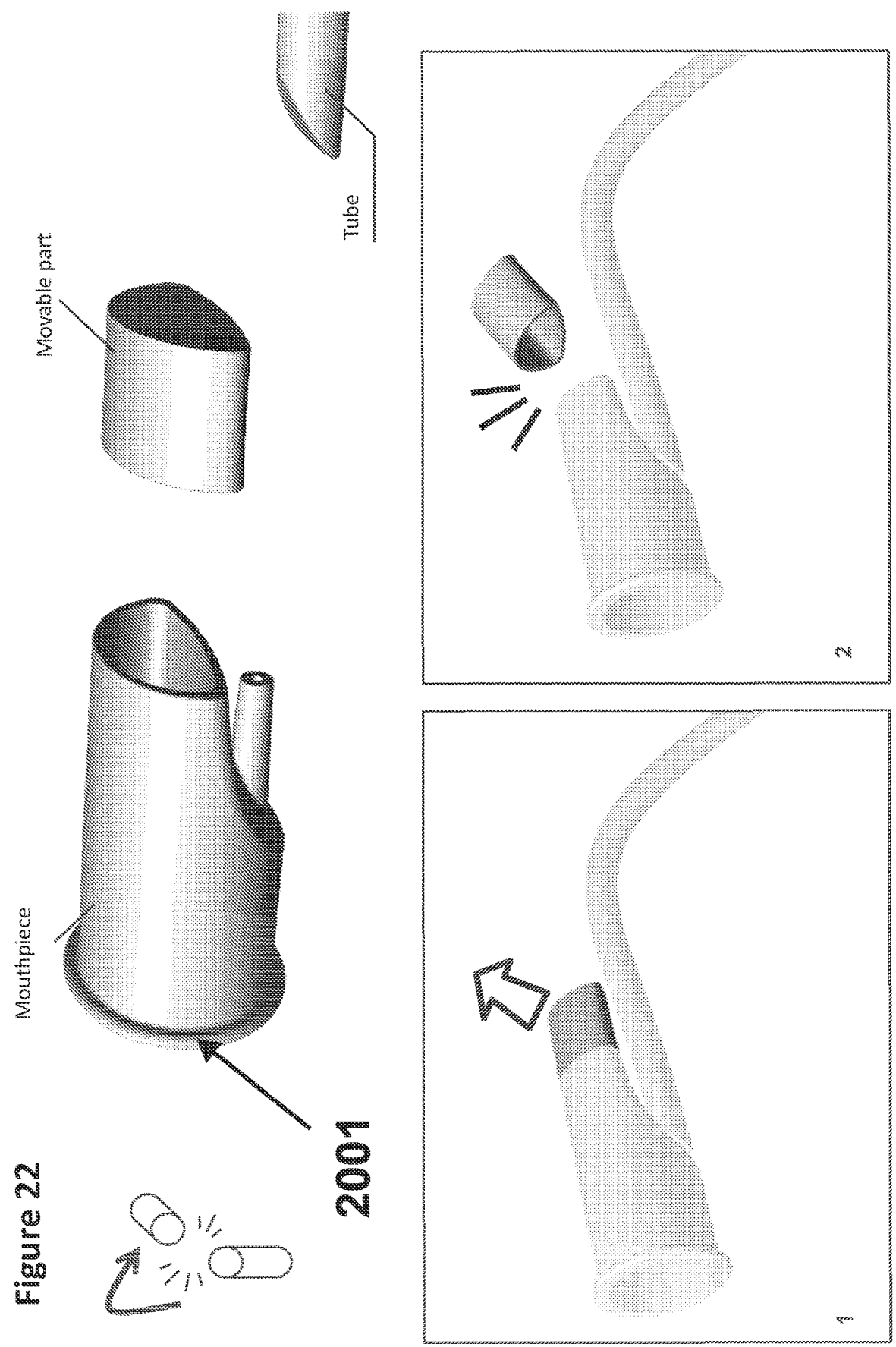
Figure 23:
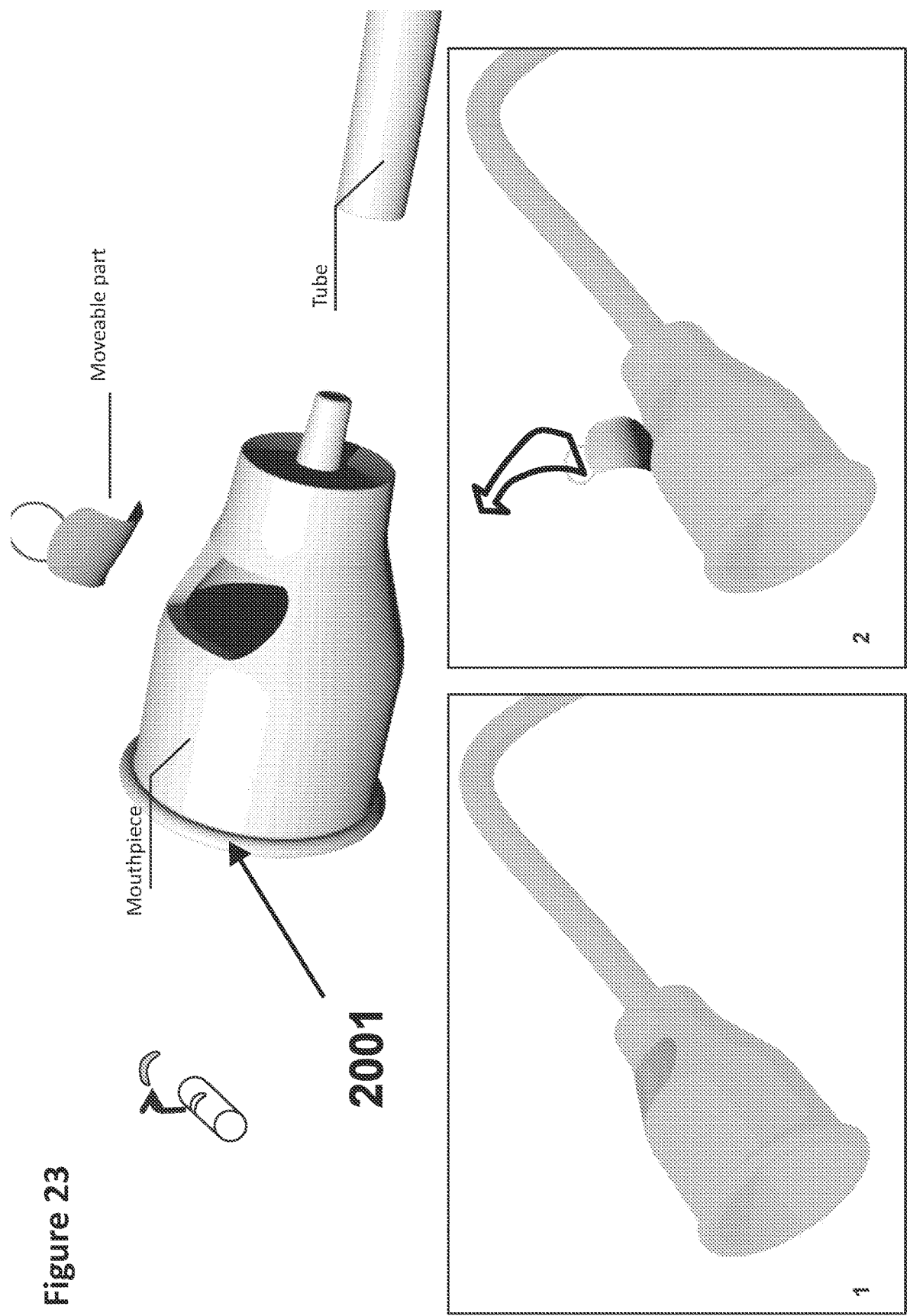

FIGS. 21 to 23 shows different designs of the mouthpiece. In FIG. 21, the mouthpiece has a movable part that can be removed from the air inlet 2001 by twisting. In FIG. 22, the mouthpiece has a movable part that can be removed from the air inlet 2001 by breaking the movable part off. In FIG. 23, the mouthpiece has a movable part that is a breakable or removable seal. When the movable part is removed, an opening is created and the opening is connected to the air inlet 2001.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising two interchangeable and independent coated electrocardiogram (ECG) electrodes, wherein the ECG electrodes form a part of the housing of a device, wherein each ECG electrode comprises at least a first sub-electrode and a second sub-electrode;
    wherein the first sub-electrode and the second sub-electrode are separately addressable;
    wherein the first sub-electrode and the second sub-electrode are separated by an insulating portion of the housing which is not coated;
    wherein the device is configured to collect ECG data from both hands of a person when each hand is in contact with one of the two independent coated ECG electrodes; wherein each of the first sub-electrode and the second sub-electrode comprises a coating that is an integral part and present at an exterior of the housing of the device; wherein the coating functions as interchangeable and disposable ECG electrodes; wherein the coated ECG electrodes comprises a plurality of layers, wherein at least a layer of the plurality of the layers comprises silver colloidal metal particles, wherein the silver colloidal metal particles are present in a liquid or a gel,
    wherein the device has a provision for a tab to connect an external mouthpiece configured to perform a cardioreflex test; and wherein the device is configured to enable the person to operate the mouthpiece when both the hands of the person are positioned on the two independent coated ECG electrodes.

2. The device of claim 1, further comprising electrical contacts configured to electrically connect the first sub-electrode and the second sub-electrode to a point-of-care device.

3. The device of claim 1, wherein the first sub-electrode and the second sub-electrode comprise an electrically conductive film on an electrically insulating substrate.

4. The device of claim 3, wherein the electrically insulating substrate is plastic.

5. The device of claim 3, wherein the insulating portion is a portion of the electrically insulating substrate not coated with the electrically conductive film.

6. The device of claim 1, wherein the first sub-electrode and the second sub-electrode comprise partial cylindrical films.

7. The device of claim 1, wherein the first sub-electrode and the second sub-electrode comprise a film of AgCl supported on a substrate with an adhesive in between.

8. The device of claim 7, wherein the adhesive comprises a layer of copper.

9. The device of claim 1, wherein the device is configured to make one or more measurements, wherein the one or more measurements comprise ECG measurements.

10. The device of claim 9, wherein the device is configured to be a component of a closed-loop system that is configured to be calibrated via the one or more measurements.

11. The device of claim 1, wherein each of the first sub-electrode and the second sub-electrode of the ECG electrodes comprising the plurality of layers comprises a second layer, a third layer and optionally a first layer, wherein each of the plurality of layers comprises a metallic material, wherein the first layer is configured to bond to a housing of the device; the second layer comprises a primer electrode; and the third layer comprises an electrode material and the third layer is configured for improving the impedance matching between the coated ECG electrodes and a measuring objective.

12. The device of claim 11, wherein the first layer comprises Cu.

13. The device of claim 11, wherein the second layer comprises the primer electrode comprising Ag and the third layer comprising an electrode material comprising Ag/AgCl.

14. The device of claim 11, wherein the device comprises the first layer.

15. The device of claim 11, wherein the third layer comprising electrode material is configured to be a disposable tape.

16. The device of claim 11, wherein the coating comprises a PVD coating technology.

17. The device of claim 11, wherein the device is further configured to be incorporated or embodied into any material comprising metal, foam, rubber, textile, or plastic.

18. The device of claim 11, wherein the device is configured to be an integral part of an apparatus for acquiring a signal related to an autonomic nervous system.

19. The device of claim 11, is further configured to be disposable.

20. The device of claim 11, wherein the device is configured to be used in applications of biological electrode systems or configured to be integrated into exercise equipment, controllers, or video game consoles.

* * * * *